US011252965B2

(12) United States Patent
Scheel et al.

(10) Patent No.: US 11,252,965 B2
(45) Date of Patent: Feb. 22, 2022

(54) RNAI INSECTICIDE MATERIALS AND METHODS

(71) Applicants: Indiana University Research and Technology Corporation, Indianapolis, IN (US); University of Notre Dame du Lac, South Bend, IN (US)

(72) Inventors: Molly Duman Scheel, Granger, IN (US); David W. Severson, Cassopolis, MI (US); Kathleen Eggleson, South Bend, IN (US); Na Wei, South Bend, IN (US)

(73) Assignees: Indiana University Research and Technology Corporation, Indianapolis, IN (US); University of Notre Dame Du Lac, South Bend, IN (US)

( * ) Notice: Subject to any disclaimer, the term of this patent is extended or adjusted under 35 U.S.C. 154(b) by 0 days.

(21) Appl. No.: 16/316,847

(22) PCT Filed: Jul. 13, 2017

(86) PCT No.: PCT/US2017/041919

§ 371 (c)(1),
(2) Date: Jan. 10, 2019

(87) PCT Pub. No.: WO2018/013801

PCT Pub. Date: Jan. 18, 2018

(65) Prior Publication Data

US 2019/0297879 A1 Oct. 3, 2019

Related U.S. Application Data

(60) Provisional application No. 62/361,704, filed on Jul. 13, 2016.

(51) Int. Cl.

| | |
|---|---|
| ***C12N 15/113*** | (2010.01) |
| ***C12N 15/81*** | (2006.01) |
| ***A01N 57/16*** | (2006.01) |
| ***A01K 67/033*** | (2006.01) |
| ***A01N 25/00*** | (2006.01) |
| ***A01N 25/02*** | (2006.01) |
| ***A01N 25/10*** | (2006.01) |
| ***A01N 63/60*** | (2020.01) |

(52) U.S. Cl.

CPC .......... *A01N 57/16* (2013.01); *A01K 67/0333* (2013.01); *A01N 25/00* (2013.01); *A01N 25/006* (2013.01); *A01N 25/02* (2013.01); *A01N 25/10* (2013.01); *A01N 63/60* (2020.01); *C12N 15/113* (2013.01); *C12N 15/81* (2013.01); *C12N 2310/14* (2013.01)

(58) Field of Classification Search

CPC .... A01N 25/006; A01N 25/02; C12N 15/113; C12N 2310/14

See application file for complete search history.

(56) References Cited

U.S. PATENT DOCUMENTS

| | | | | |
|---|---|---|---|---|
| 8,759,306 | B2 | 6/2014 | Kaletta | |
| 8,841,272 | B2 | 9/2014 | Zhu et al. | |
| 8,933,042 | B2 | 1/2015 | Raemaekers et al. | |
| 9,290,764 | B2 | 3/2016 | Kaletta | |
| 2005/0255487 | A1* | 11/2005 | Khvorova .......... | C12N 15/1048 435/6.11 |
| 2012/0053231 | A1* | 3/2012 | Paldi ...................... | A61K 31/00 514/44 A |
| 2019/0037854 | A1* | 2/2019 | Chiu ...................... | A01N 63/30 |

FOREIGN PATENT DOCUMENTS

WO 2015170324 A2 11/2015

OTHER PUBLICATIONS

Seok et al., (Mol. Cells 2016; 39(5): 375-381) (Year: 2016).*
Jackson et al., (Nature Biotechnology 21(6): 635-637, 2003) (Year: 2003).*
Pertea et al (bioRxiv 332825; doi: https://doi.org/10.1101/332825, 2017, 21 pages) (Year: 2017).*
GEnBank NM_007158.3, 2004 retrieved from, https://www.ncbi.nlm.nih.gov/nuccore/NM_007158.3 (Year: 2004).*
GenBank AW025184, 2011 retrieved from https://www.ncbi.nlm.nih.gov/nuccore/AW025184.1 (Year: 2011).*
GenBank NM_018913.3, 2020, retrieved from https://www.ncbi.nlm.nih.gov/nuccore/NM_018913.3 (Year: 2020).*
NCBI XM_021838825.1 (Year: 2017).*
NCBI XM_039576472.1 (Year: 2021).*
NCBI XM_035931293.1 (Year: 2020).*
Extended Search Report issued by the European Patent Office, dated Jul. 13, 2020, for European Patent Application No. 17828458.4; 9 pages.
Keshava Mysore, et al., "Chitosan/siRNA nanoparticle targeting demonstrates a requirement for single-minded during larval and pupal olfactory system development of the vector mosquito Aedes aegypti", BMC Developmental Biology 2014, 14.9, http://www.biomedcentral.com/1471-213X/14/9; 16 pages.
Keshava Mysore, et al., "SiRNA-Mediated Silencing of doublesex during Female Development of the Dengue Vector Mosquito Aedes aegypti", PLOS Neglected Tropical Diseases, Nov. 6, 2015; 21 pages.
Keshava Mysore, et al., "Disruption of Aedes aegypti Olfactory System Development through Chitosan/siRNA Nanoparticle Targeting of semaphorin-1a", PLOS Neglected Tropical Diseases, May 2013, vol. 7, Issue 5; 12 pages.

(Continued)

*Primary Examiner* — Richard A Schnizer
(74) *Attorney, Agent, or Firm* — Faegre Drinker Biddle & Reath LLP

(57) ABSTRACT

The present invention provides a novel class of insecticides for control of disease vector insects, particularly mosquitoes. These insecticides prevent maturation or development of larvae into adult insects using interfering RNA (iRNA). The present invention further includes compositions comprising iRNA and methods of controlling, reducing, or treating an insect infestation with the iRNA or compositions described herein.

14 Claims, 7 Drawing Sheets

Specification includes a Sequence Listing.

(56) References Cited

OTHER PUBLICATIONS

Xin Zhang, et al., "Chitosan/Interfering RNA Nanoparticle Mediated Gene Silencing in Disease Vector Mosquito Larvae", JOVE Journal of Visualized Experiments, Mar. 2015, 97; 11 pages.
Clemons, A, Haugen, M., Severson, D., and M. Duman-Scheel (2010). "Functional analysis of genes in Aedes aegypti embryos." Cold Spring Harb Protoc 2010(10): pdb prot5511.
Kumar, A, Wang, S., Ou, R., Samrakandi, M., Beemtsen, B.T., and Sayre, R.T. (2013). Development of an RNAi based microalgal larvicide to control mosquitoes. MW Journal. 4:6 (GCE Special Issue).
Kweka, E.J., Zhou, G., Munga, S., Lee, M.C., Atieli, H.E., Nyindo, M., Githeko, AK., and Yan, G. (2012). Anopheline larval habitats seasonality and species distribution: a prerequisite for effective targeted larval habitats control programmes. PLoS One. 7(12):e52084.
Merritt, R.W. (1992). "Feeding behaviour, natural food, and nutritional relationships of larval mosquitoes." Ann. Rev. Entomol. 37: 349-376.
Mumberg, D., Muller, R., and Funk, M. (1995). "Yeast vectors for the controlled expression of heterologous proteins in different genetic backgrounds." Gene 156: 119-122.
Mysore, K., E. M. Flannery, M. Tomchaney, D. W. Severson and M. Duman-Scheel (2013). "Disruption of Aedes aegypti olfactory system development through chitosan/siRNA nanoparticle targeting of semaphorin-la." PLoS Negl Trop Dis 7(5): e2215.
Mysore, K., E. Andrews, P. Li and M. Duman-Scheel (2014a). "Chitosan/siRNA nanoparticle targeting demonstrates a requirement for single-minded during larval and pupal olfactory system development of the vector mosquito Aedes aegypti." BMC Dev Biol 14: 9.
Mysore, K., E. Flannery, M. T. Leming, M. Tomchaney, L. Shi, L. Sun, J.E. O'Tousa, D. W. Severson and M. Duman-Scheel (2014b). "Role of semaphorin-1a in the developing visual system of the disease vector mosquito Aedes aegypti." Dev Dyn 243(11): 1457-69.
Dolan DNA Learning Center, Cold Spring Harbor Laboratory, Silencing Genomes (© 2006). "Creating an RNAi feeding strain." http://www.silencinggenomes.org/downloads/pdfs/mai_feeding_strain.pdf, accessed Jun. 2015.
Van Ekert, E., C. A Powell, R. G. Shatters Jr., and D. Borovsky. "Control of larval and egg development in Aedes aegypti with RNA interference against juvenile hormone acid methyl transferase." J Insect Physiol 70: 143-150. WHO (2005). "Guidelines for laboratory and field testing ofmosquito larvicides." http://whqlibdoc.who.int/hq/2005/who_eds_whopes_gcdpp_2005.13.pdf, accessed Sep. 2014.
Whyard, S., C. N. Erdelyan, A L. Partridge, A D. Singh, N. W. Beebe, and R. Capina (2015). "Silencing the buzz: a new approach to population suppression of mosquitoes by feeding larvae double-stranded RNAs." Parasit Vectors 8: 96.
Zhang, X., J. Zhang and K. Y. Zhu (2010). "Chitosan/double-stranded RNA nanoparticle mediated RNA interference to silence chitin synthase genes through larval feeding in the African malaria mosquito (*Anopheles gambiae*)." Insect Mol Biol 19(5): 683-693.
Mysore et al. "siRNA-Mediated Silencing of doublesex during Female Development of the Dengue Vector Mosquito Aedes aegypti," PloS Neglected Tropical Diseases, DOI:10.1371, Nov. 6, 2015, vol. 9, No. 121, e0004213, pp. 1-21.
International Search Report and Written Opinion issued by the ISA/US, Commissioner for Patents, dated Oct. 2, 2017 for International Application No. PCT/US2017/041919.
International Preliminary Report on Patentability, issued by The International Bureau of WIPO, Geneva, Switzerland, dated Jan. 15, 2019, for International Application No. PCT/US2017/041919.
Economou, Chloe, et al. "A Simple, Low-Cost Method for Chloroplast Transformation of the Green Alga Chlamydomonas reinhardtii" Pal Maliga (ed.), Chloroplast Biotechnology; Methods and Protocols, Methods in Molecular Biology, vol. 1132, 2014; 11 pages.
Singh, Aditi D., et al. "Oral delivery of double-stranded RNA in larvae of the yellow fever mosquito, Aedes aegypti: Implications for pest mosquito control", Journal of Insect Science, vol. 13, article 69, 2013; 18 pages.
Zhang, Xin, et al. "Chitosan/Interfering RNA Nanoparticle Mediated Gene Silencing in Disease Vector Mosquito Larvae", Journal of Visualized Experiments, Mar. 2015; 11 pages.

* cited by examiner

Fig. 7
UNITED STATES OF AMERICA
ONE CENT

RNAI INSECTICIDE MATERIALS AND METHODS

CROSS-REFERENCE TO RELATED APPLICATIONS

This application represents the U.S. National Stage of International Application No. PCT/US2017/041919, filed Jul. 13, 2017, which claims priority to U.S. Provisional Application No. 62/361,704, filed Jul. 13, 2016, which is incorporated herein as if set forth in its entirety.

STATEMENT REGARDING FEDERALLY SPONSORED RESEARCH OR DEVELOPMENT

N/A

BACKGROUND OF THE INVENTION

Mosquito-borne infectious diseases continue to be a serious global health concern. For example, malaria, which is caused by parasites transmitted by anopheline vector mosquito species, was responsible for 198 million clinical cases and over 500,000 deaths in 2013, per World Health Organization estimates. Media coverage of the ongoing Zika outbreak in South America, with its correlation to microcephaly in babies and Guillain-Barré Syndrome, both of which can require intensive medical intervention, have caused considerable alarm in the U.S. and worldwide, igniting renewed interest in combating mosquito-borne infectious disease. Viruses that cause Zika, chikungunya, yellow fever, as well as dengue, the most widespread and significant arboviral disease in the world, are spread by the bite of the vector mosquito in the genus *Aedes*, chiefly *A. aegypti* but also *A. albopictus*. Zika cases, which are linked to severe birth defects and neurological disorders, are currently occurring in many countries in the Americas, including Belize. *Aedes aegypti* and *Aedes albopictus*, the principle vectors of Zika virus, lay eggs in natural and artificial water-filled containers located within or close to human dwellings. Due to these significant health concerns, the World Health Organization recently designated Zika virus an international public health emergency (WHO, 2016). Furthermore, dengue, the most widespread and significant arboviral disease in the world, is a threat to >2.5 billion people in the tropics, including the southern continental United States, Hawaii, and Puerto Rico. Dengue has an annual incidence of approximately 400 million cases resulting in ~50,000 deaths annually worldwide (WHO, 2016). These statistics highlight the critical need to combat these viruses and their mosquito vectors. Given poor progress in vaccine development and distribution, mosquito control is the primary mechanism for disease control. However, the emergence of insecticide resistance and a lack of support for mosquito control programs compromise current strategies for managing mosquitoes (CDC, 2014).

Dozens of species in the genus *Anopheles* transmit protozoan parasites in the genus *Plasmodium*, which cause malaria. Multiple forms of encephalitis, dog heartworm, and West Nile virus are also transmitted by mosquitoes. Together, these mosquito-borne diseases kill over a million people, and sicken hundreds of millions, every year.

Given poor progress in vaccine development and distribution, mosquito control is the primary mechanism for disease control, but our existing arsenal for eliminating mosquitoes is not adequate. *A. aegypti* lay eggs in water-holding containers, including natural plant containers, as well as a variety of man-made artificial containers that collect rain water or that are filled with water by humans. Larvae hatch from the eggs and remain in the water-filled containers through the end of the pupal stage. During this aquatic phase, the immature mosquitoes are concentrated in defined water boundaries and therefore susceptible to control efforts, including larviciding. Larviciding, the application of microbial or chemical agents to kill mosquito larvae before they are reproducing adults that vector human disease, is a mechanism for larval source management (LSM) and is a key component of integrated *A. aegypti* control strategies (CDC, 2014). Temephos, a relatively inexpensive pesticide used globally, is one of the few organophosphates approved for control of *A. aegypti* larvae (EPA, 2001). Temephos attached to silica (sand) granules, the active ingredient in Abate®, has been used to treat large water containers that are too large to empty (BASF, 2014). However, after >30 years of heavy temephos usage, temephos resistant *A. aegypti* strains have been identified in many countries (Mazzarri and Georghiou, 1995; Saavedra-Rodriguez et al., 2013). In a recent reregistration eligibility decision, the EPA called for labeling changes to address risks that temephos poses to human and environmental health and also prohibited drinking water source treatment (EPA, 2015a). Methoprene, a growth regulator widely used for *Aedes* larval control, can be applied to water surfaces or delivered in slow-release briquettes (Rozendaal, 1997). Although methoprene does not pose unreasonable risks to human health, it is extremely toxic to other invertebrate species (EPA, 2000), and reduced susceptibility/resistance has begun to emerge (Marcombe et al., 2014; Lau et al., 2015). Due to the frequent development of pesticide resistance and growing concerns about the nontarget effects of pesticides in the environment, the current pesticide repertoire will soon reach its expiration date. Larviciding is also used as a method for controlling malaria vector mosquitoes. Although insecticide treated nets (ITNs) and indoor residual spraying (IRS) are the backbone for malaria vector control, there is increasing interest in the use of LSM for reduction of residual malaria transmission. Integrated control programs which included larviciding were successful in Tanzania, Sudan, and Mauritius, and the World Health Organization (WHO) recommended that larviciding, when used as a supplement to ITNs and IRS in sub-Saharan Africa, is cost-effective for malaria control in urban settings where vector breeding sites are few, fixed, and findable. Given the renewed interest in larviciding, frequent development of insecticide resistance, and rising concern for the non-target effects of pesticides, the current larvicide repertoire will soon reach its expiration date. The continued practice of larviciding will require generation of new environmentally safe larvicides. The development of new larvicides with minimal impact on the environment is therefore essential and urgent (Whyard et al., 2009).

Insecticide resistance is increasing, rendering some of the current insecticide options useless. Also, concern about the non-target effects of some pesticides (most notoriously, DDT), limits their practical utility. The current pesticide repertoire will soon reach its expiration date, and the need to develop a new generation of environmentally safe options is urgent.

Larviciding, the application of microbial or chemical agents to kill mosquito larvae in aquatic habitats, is therefore a key component of integrated *Aedes* and *Anopheles* control and disease prevention strategies (WHO). Given the increase of reported insecticide resistance to existing larvicides and the rising concern for negative effects of pesticides on non-target organisms, the current larvicide repertoire is faced with great challenges to sustainability.

New larvicidal agents are vitally needed to address emerging arthropod-borne infectious diseases such as Zika and to target mosquito populations. While a number of recent patents have suggested the use of RNA interference for controlling insect and other pests, generally describing use of RNAi, none have disclosed the new high throughput screen for the selection of larval-lethal genes in mosquitoes including the effective siRNAs that are conserved among different mosquito species but not humans or the specific sequences identified in the present invention. For example, U.S. Pat. No. 8,933,042 entitled "Methods for Controlling Pests Using RNAi" discloses the use of RNA interference for controlling pest infestations, and generally discloses mosquitoes in a laundry list of pests. U.S. Pat. Nos. 9,290,764 and 8,759,306 entitled "RNAi for the Control of Insects and Arachnids" discuss and disclose RNAi that target insects, including mosquitoes but do not discuss the screening for mosquito larva-lethal genes, efforts to design iRNA larvicides that target sequences conserved in multiple arthropod pests but not in non-target species, or the specific sequences as described herein. As the Anopheline genomes have only been recently reported, prior studies were not able to determine target sequences conserved between multiple different mosquito species (e.g. *Aedes* and *Anopheles*) (Neafsey et al 2015).

BRIEF SUMMARY OF THE INVENTION

The present invention provides at least one interfering ribonucleic acid (iRNA) able to target and silence expression of at least one gene required for maturation from larva to adult of at least one insect, preferably a mosquito. In some aspects, the at least one synthetic iRNA is able to target and silence at least one gene required for adult mosquito survival.

In another aspect, the present invention provides a DNA construct encoding and able to express at least one iRNA able to target and silence expression of at least one gene required for maturation from larva to adult of at least one insect, preferably a mosquito. In some aspects, the at least one gene is required for adult mosquito survival.

In another aspect, the present invention provides a host cell engineered to express at least one ANA able to target and silence expression of at least one gene required for maturation from larva to adult of at least one insect, preferably a mosquito. In some aspects, the host cell is a yeast cell.

In another aspect the present invention provides a mosquito larvicide composition for preventing and/or controlling mosquito infestation comprising at least one interfering ribonucleic acid (ANA) able to target and silence expression of at least one gene required for maturation from larva to adult of at least one insect and/or able to target and silence expression of at least one gene required for survival of an adult insect, preferably a mosquito, a host cell expressing the iRNA, a bacterial cell expressing the iRNA, or a yeast cell expressing the iRNA, and at least one suitable carrier, excipient or diluent.

A further aspect provides a method for controlling, reducing or treating an insect infestation comprising exposing; at least one insect to the at least one interfering ribonucleic acid (iRNA) able to target and silence expression of at least one gene required for maturation of the at least one insect from larvae to adult and/or required for survival of an adult insect, preferably a mosquito, or a composition comprising at least one iRNA in an effective amount to control, reduce or treat the insect infestation. In a preferred embodiment, the insect infestation is a mosquito infestation. In some embodiments, the at least one insect is an insect larva.

DETAILED DESCRIPTION OF THE INVENTION

Figure 1:
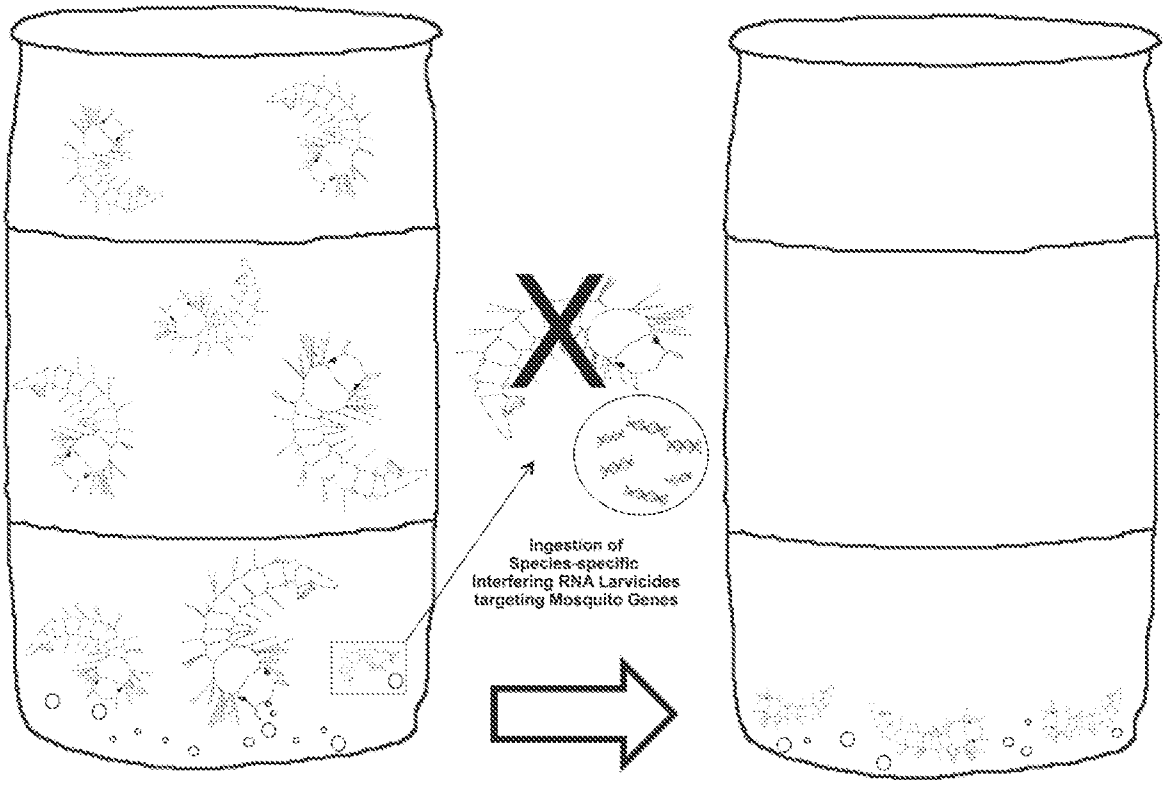
FIG. 1 is a schematic of the depiction of the present invention.

The present disclosure provides a new class of insecticides for control of disease vector mosquitoes. The insecticides target juvenile mosquitoes, preventing their maturation into reproducing adults that can spread disease-causing pathogens, and in some embodiments, the insecticide can also target and kill adult mature mosquitoes. The insecticides can kill mosquitoes at multiple stages of their development. These insecticides use synthetic small interfering RNAs (siRNAs) and their short hairpin RNA (shRNA) counterparts to selectively target genes in developing mosquito larvae and/or adult mosquitoes. The short length of this interfering RNA facilitates the design of insecticides that target multiple species of mosquitoes, but which do not correspond to sequences in the human genome or other non-targeted species. By identifying multiple interfering RNA target sites in mosquito larval genes, we have created an insecticide arsenal to combat resistance arising from point mutations in any one target sequence.

The present inventions provides a means for controlling mosquito infestations by exposing the juvenile mosquito to a interfering RNA sequence that suppresses or inhibits a gene required for maturation or development of the juvenile mosquito (e.g. larva) into an adult mosquito. Such means, as described herein, include, an insecticide or a larvicide, for example, iRNA, RNA constructs and compositions which result in the desired suppression or inhibition of a gene needed for growth, development or maturation. The targeted gene may also play a role in the survival of mature adult mosquitoes, allowing for the ability to target and kill mosquitoes at any life stage.

The present disclosure provided a high-throughput method of screening for larval lethal genes that can be used as a target for iRNA to suppress or inhibit maturation and development of larvae into adults. Larval lethal genes refer to target genes that result in the death or the inhibition of maturation of a larva to an adult in a target arthropod, for example, insects, preferably a mosquito. The method may suitably be used to screen for larva-lethal gene of arthropods, including insect species, for example, mosquitoes, filter feeding pest species, including, for example, members bellowing to the order diptera (fly), trichptera (caddisfly), enphymeroptera (mayfly), and the like. The method of uptake of the iRNA will depend on the particular species targeted. The siRNA can then be formulated into compositions for topically-applied or orally delivered formulations.

A similar screening for adult lethal genes is also provided. In one embodiment, genes identified as larval lethal are tested to see if they are also adult lethal. Adult lethal genes refer to target genes that are essential for adult mosquito survival and results in the death of mature adult mosquitoes.

The present invention provides at least one interfering ribonucleic acid (iRNA) able to target and suppress at least one gene required for maturation and/or growth from larva to adult of at least one arthropod, for example, an insect, preferably a mosquito species (e.g. larva-lethal gene).

In some embodiments, the at least one iRNA is able to target and suppress at least one gene required for survival of at least one insect at any life stage, i.e. larval and/or adult. Some iRNA are thus able to target the insect (e.g. mosquito) at any stage within the life cycle resulting in suppression of growth and/or survival.

In one embodiment, the screen for larval lethal genes for *Aedes aegypti* found genes that are expressed during all four larval instars. Thus, siRNA designed to target these larval lethal genes are able to target larvae at any of the four larval instar stages which has not previously been described. Further, in some embodiments, these larval lethal genes are also adult lethal genes required for adult mosquito survival, and thus are siRNA that can target mosquitoes at any life stage.

The term "iRNA" refers to ribonucleic acid (RNA) sequences and constructs that are able to operate within the RNA interference (RNAi) pathway by interfering with transcriptional or post-transcriptional gene expression resulting in reduced or inhibited expression of a specific gene. For purposes herein, the term "iRNA" refers to short interfering RNA (siRNA), short hairpin RNA (shRNA) and double stranded RNA (dsRNA) that operate within the RNAi pathway. In some instances, the iRNA in produced within a cell via a DNA construct that expresses said iRNA. The iRNA of the present invention are synthetic and can be expressed in a vector or host cell in which the iRNA is not normally expressed. For example, the siRNA may target an insect gene, e.g. a mosquito gene and be expressed by a exogenous vector or expressed in a bacterial or yeast cell that does not naturally contain the target gene or target sequence to which the siRNA binds. The iRNA may be modified in a manner that alters the iRNA properties in order to be exogenously expressed by the host cell, e.g. the siRNA or the complementary sequence use to express the iRNA may be modified at its ends or incorporated into an exogenous sequence in order to be able to be expressed in the target host cell. In some embodiments, the iRNA is operably linked to an exogenous sequence that allows for its expression.

siRNA, sometimes referred to as small interfering RNA, short interfering RNA or silencing RNA are short double-stranded RNA molecules of <30 base pairs in length, for example, about 19-30 base pairs in length that operate through the RNAi pathway. Each siRNA is unwound into two single-stranded RNAs (ssRNAs), one of which is incorporated into the RNA-induced silencing complex (RISC) leading to post-transcriptional gene silencing. SiRNAs can be generated in several ways. In some cases, long dsRNA is introduced to a cell, either by a virus, endogenous RNA expression (i.e., microRNA), or exogenously delivered dsRNA. The enzyme Dicer cleaves the long duplex RNAs into siRNAs. Another way to introduce siRNA into cells is to express shRNA from plasmid vectors. Alternatively, siRNA duplexes can be chemically synthesized, mimicking the structure of Dicer-processed products, are commonly used in research for gene silencing. Chemically synthesized siRNAs simply bypass the Dicer cleavage step. In some preferred embodiments, the iRNA are about 25 bp in length.

shRNA are artificial single-stranded RNAs having a secondary structure such that a portion of the RNA strand forms a hairpin loop. The terminology short hairpin RNA and small hairpin RNA are encompassed by shRNA. Expression of shRNA in cells is typically accomplished by delivery of DNA construct to the cell, e.g. through an expression vector. shRNA is transcribed under the control of RNA Pol-II or Pol-III promoters, and folds into a structure resembling a siRNA duplex. shRNAs are then processed by Dicer into siRNAs.

dsRNA refers to long double-stranded RNA molecules that are cleaved by the enzyme Dicer into short double-stranded fragments of about 20-25 nucleotide siRNAs.

RNA interference (RNAi) or Post-Transcriptional Gene Silencing (PTGS) refers to the biological process in which RNA molecules interfere or inhibit the expression of specific genes with complementary nucleotide sequences to the iRNA (gene-specific suppression of gene expression). RNAi results in the degradation of mRNA after transcription, resulting in no translation and protein expression.

"Gene suppression" or "down-regulation of gene expression" or "inhibition or suppression of gene expression" are used interchangeably and refer to a measurable or observable reduction in gene expression or a complete abolition of detectable gene expression at the level of protein product ("gene silencing"), and/or mRNA product from the gene. In some embodiments, gene suppression results in gene silencing, referring to the ability of the iRNA to target mRNA for degradation, resulting in no translation and therefore no protein expression. The ability of the iRNA to suppress or down-regulate at least one gene leads to the suppression or inhibition of the mosquito's growth or maturation or death of the mosquito larvae or adult mosquito. The down-regulation or inhibition may occur at the translational or post-translational stage of expression of the gene of interest by promoting transcript turnover, cleavage or disruption of translation.

A gene refers to a polynucleotide sequence that comprises control and coding sequences necessary for the production of a polypeptide (protein). The polypeptide can be encoded by a full length coding sequence or by any portion of the coding sequence. A gene may be an uninterrupted coding sequence or may include one or more introns contained between splice junctions. As used herein, a gene may include variants of the gene, which include, but are not limited to, modifications such as mutations, insertions, deletions or substitutions of one or more nucleotides. The target gene is the gene targeted for down-regulation or suppression by the iRNA of the present technology.

The reduction, inhibition or suppression of expression of the target gene results in the inability of the larvae to mature into an adult arthropod insect, e.g., mosquito. The target gene required for maturation and/or growth refers to a gene necessary for the survival, growth, or development of larvae into an adult and may ultimately result in larvae or pupae death. The gene may inhibit the ability of the larvae to develop into pupae, of pupae from developing into adults, or any intervening developmental step. In some instances, the inhibition or suppression of the target gene results in the inability of an adult insect to survive.

Down-regulation or inhibition of gene expression in cells of the mosquito can be confirmed by phenotypic analysis of the cell or the whole mosquito, for example death of the mosquito larva, pupa or adult mosquito (which can be quantitated, for example, as a % mortality). Suitably, the iRNA or compositions provide a % mortality of at least about 50%, alternatively at least about 60%, alternatively at least about 70%, alternatively at least about 75%, alternatively at least about 80%, at least about 90%, alternatively at least about 95%, alternatively at least about 98%, alternatively at least about 100%, and any and all numerical values and ranges in between.

Other methods of confirming down-regulation of the gene expression are known in the art, and include, but are not limited to, measurement of mRNA or protein expression using molecular techniques such as RNA solution hybridization, nuclease protection, Northern hybridization, reverse transcription, gene expression monitoring with a microarray, antibody binding, enzyme-linked immunosorbant assay (ELISA), Western blotting, radioimmunoassay (MA), other immunoassays, or fluorescence-activated cell analysis (FACS) and the like.

In some embodiments, the effectiveness of larvicide is characterized by the lethal concentrations (LC) for mortality and inhibition of adult emergence (IE). In some embodiments, the effectiveness of the insecticide is characterized by the lethal concentration or lethal dose (LD) for an adult insecticide.

The term juvenile mosquito, as referred to herein, refers to the stages of the mosquito life cycle before it becomes an adult but after hatching from an egg. Juvenile mosquito can refer to the larva or pupa stage.

Suitable target genes for use in the present invention include genes identified as larval lethal genes in one or more species of mosquito, as described herein. Larval lethal genes are genes that result statistically significant lethality when compared to a control siRNA treatment. In some embodiments, the larval lethal genes resulted in at least 50% mortality of larvae. In some embodiments, larval lethal genes result in at least 60% mortality, alternatively at least 70% mortality, alternatively at least 80% mortality, alternatively at least 90% mortality, alternatively at least 95% mortality, alternatively 100% mortality. Another suitable method to measure mortality is described in the WHO (2005) guidelines for larvicide testing, incorporated by reference in its entirety.

Additional suitable genes for use in the present invention include genes identified as adult lethal genes for one or more species of mosquitoes. Adult lethal genes are genes that result in statistically significant lethality when compared to a control siRNA treatment. In some embodiments, the adult lethal genes result in at least 60% mortality, alternatively at least 70% mortality, alternatively at least 80% mortality, alternatively at least 90% mortality, alternatively at least 95% mortality, alternatively 100% mortality. In some embodiments, the larval lethal gene is also an adult lethal gene.

In some embodiments, the iRNA inhibit gene expression and result in larvae death or inhibition of maturation of at least two insects, preferably at least two mosquito species, in some embodiments, at least three insects, preferably at least three mosquito species, in further embodiments, at least four insects, preferably at least four mosquito species, in further embodiments at least five insects, preferably at least five mosquito species.

In some embodiments, the iRNA inhibits gene expression and results in larvae death or inhibition of maturation of the larva and adult death of at least two insect species, alternatively at least three insect species, alternatively at least four insect species, alternatively at least five insect species. In preferred embodiments, the insect species are mosquito species.

Suitable targets of the present technology are insects, preferably mosquitoes, flies, caddisfly, mayfly and the like. Suitable mosquito species include, by are not limited to, mosquitoes found in the genus *Aedes, Anopheles, Culex, Ochlerotatus, Culiseta, Psorophora, Coquilletitidia*, and *Mansonia*. Suitable members of the order Diptera (fly), include, but are not limited to, for example, members of the families Nematocera and Brachycera. Suitable members of the order Trichoptera, include, but are not limited to, members belonging to the superfamilies Hydropsychoidea, Hydroptiloidea, Leptoceroidea, Limnephiloidea, Necrotauliodea, Phiopotamoidea, Phryganeoidea, Pryacophiloidea, Sericostomatoidea, Vitimotauiodeal. Suitable members of the order Ephymeroptera are known in the art, and include, but are not limited to, the superfamily Ephemerelloidea, Caenoidea, Baetoidea, Heptagenioidea, Leptophlebioidea, Ephemeroidea and the like.

Suitable mosquitoes that belong to the genus *Anopheles* include, but are not limited to, for example, *An. aconitus, An. albimanus, An. albitarsis s.l., An. annularis, An. aquasalis, An. arabiensis, An. atroparvus, An. coluzzii, An. arabiensis, An. balabacensis, An. barberi, An. barbitrosstris* s.l., *A. bellator, A. crucians, An. cruzii, An. culicifacies s.l., An. darlingi, An. dirus* s.l., *A. earlei, An. farauti* s.l., *An. flavirostris, An. fluviatilis s.l., An. freeborni, An. funestus, An. gambiae, A. gambiae* (Giles 1902), *An. introlatus, An. koliensis, An. labranchiae, An. latens, An. lesteri, An. leucosphyrus/lateens, An. maculates, An. maculipennis, An. marajoara, An. messeae, An. minimus* s.l., *A. moucheti, An. nili, An. nuneztovari* s.l., *An. pseudopunctipennis, A. punctipennis, An. punctulatus s.l., An. quadrimaculatus s.l., An. sacharovi, An. sergentii, An. sinensis, An. stephensi, An. subpictus, An. sundaicus* s.l., *An. superpictus, An. walker* and the like.

Suitable mosquitoes that belong to the genus *Aedes* include, but are not limited to, for example, *A. aegypti, A. albopictus, A. australis, A. cinereus, A. polynesiensis, A. rusticus, A. vexans, A. abserratus, A. atlanticus, A. atropalpus, A. brelandi, A. campestris, A. canadensis, A. cantator, A. cataphylla, A. connnunis, A. deserticola, A. dorsalis, A. dupreei, A. epacitus, A. exerucians, A. fitchii, A. falvescens, A. fulvus, A. grossbecki, A. hensilli, A. hersperonotius, A. hexodontus, A. implicatus, A. infirmatus, A. intrudens, A. melanimon, A. mitchellae, A. nigromaculis, A. provocans, A. solicitans, A. squamiger, A. sticticus, A. stimulans, A. taeniorrhynchus, A. triseriatus, A. trivittatus*, and the like.

Suitable mosquitoes that belong to the genus *Culex* include, but are not limited to, for example, *Culex annulrostris, Culex annulus, Culex pipiens, Culex quinquefascia-*

*tus, Culex sitiens, Cules tritaeniorhynchus, Culex vishnui, Culex univittatus*, among others.

Species able to transmit vector-borne illnesses, such as Zika virus, Dengue virus, malaria, etc. are preferentially targeted.

In a preferred embodiment, the at least one mosquito species includes *A. aegypti* (yellow fever mosquito). In another preferred embodiment, the at least one mosquito species includes *An. gambiae* (African malaria mosquito). In another embodiment, the at least one mosquito species includes at least one species from the genus *Aedes* and at least one species from the genus *Anopheles.*

In a preferred embodiment, the siRNA target sequences are conserved in multiple mosquito species but not conserved in non-targeted species. Through the identification and use of multiple larval lethal genes and multiple target sequences to each gene, the present invention is able to reduce, inhibit or eliminate insecticide resistance arising from a point mutation in any one target sequence. In other words, the siRNA of the present invention are designed to reduce the likelihood of producing insecticide resistant strains by combining multiple targets genes and multiple sequences within those target genes that are conserved among a number of species.

In some embodiments, the at least one mosquito species is *A. aegypti*. Suitably the iRNA targets at least one lethal gene of *A. aegypti*. Suitable lethal genes of *A. aegypti*, include, but are not limited to, the genes listed in Table 1, Table 5 and Table 6 and combinations thereof. For example, suitable target genes include, but are not limited to, at least one gene selected from the group consisting of Gene ID AAEL007292, Gene ID AAEL007298, Gene ID AAEL007548, Gene ID AAEL007546, Gene ID AAEL007554, Gene ID AAEL007563, Gene ID AAEL000032, Gene ID AAEL007876, Gene ID AAEL009273, Gene ID AAEL007718, Gene ID AAEL004874, Gene ID AAEL004756, Gene ID AAEL003517, and Gene ID AAEL014566, and a combination of any two or more of the foregoing. All gene sequences are incorporated by reference in their entireties.

In some embodiments, one or more iRNA targets a specific sequence within an *A. aegypti* lethal gene, for example, but not limited to, the specific target sequences found in Table 2 and orthologs thereof and combinations thereof. Suitable target sequences within these genes include, but are not limited to, the specific target sequences listed in Table 2 and Table 6, including, for example, CTAGCATCATCTTCCGACCGAACCA (SEQ ID NO: 1), GCACAAGTGGCATTGATAATCCTAT (SEQ ID NO:2), GTATCAGTCAGTATCAGAACCAGAA (SEQ ID) NO:3), CGCTGGTTCTGCTGAGAATCAACCG (SEQ ID NO:4), GGGAGAACAGCGACAGCAAGGAGAA (SEQ ID NO:5), GAACGACAATGCTGTATATTTGCGA (SEQ ID NO:6), CCACAAGCTGCGTCACTTCTACGAC (SEQ ID NO:7), CGAGGAGCTGAATGAGATTAAACCG (SEQ ID NO: 8), CGATGAGTCTGAAGAGATACGAATC (SEQ ID NO:9), CCTCCAGGCTGGATCGTTTGAGTTT (SEQ ID NO: 10), CGATGATGTCGGATGGGATGTCCAG (SEQ ID NO: 11), GAAGAAGTACCGTGTGGAAGTGGGA (SEQ ID NO:12), CACTGACAATGATCCGATAAAGACA (SEQ ID NO:13), GTACCTAGTCGATGGTCAATCAGAG (SEQ ID NO: 14), CATTGTTATTACTCACGATGTCAAG (SEQ ID NO: 15), GGAGAAGTGATGACCGTCATGAGAA (SEQ ID NO:16), GGACGTCATTGAAACGGATTTGCTA (SEQ ID NO: 17), GGAACTGCTAACCGATCAAGAGAAC (SEQ ID NO:18), CGTTATTACCATTACGGTAAATGGC (SEQ ID NO: 19), GGGAGGTGATAAGAAACGATGCTCT (SEQ ID NO: 20), GCAAGACAGATTTCGATAAAGATCA (SEQ ID NO:21), and combinations thereof.

In other embodiments, the at least one iRNA targets mosquitoes of the *Anopheles* genus (e.g. *Anopheles gambiae*). Suitably, the iRNA targets the at least one target gene as described in Table 3 and orthologs thereof. Other suitable target genes can be found in Table 6 and orthologs thereof. Suitable target genes include, but are not limited to, for example, a gene selected from Gene ID AGAP000891, Gene ID AGAP008903, Gene ID AGAP003014, Gene ID AGAP011489, Gene ID AGAP007987, Gene ID AGAP007596, Gene ID AGAP007254, Gene ID AGAP009777, Gene ID AGAP011133, Gene ID AGAP010510, Gene ID AGAP004548, Gene ID AGAP010265, Gene ID AGAP009978, and combinations thereof. All Accession No. sequences are incorporated by reference in their entireties. Suitably, iRNA can target the specific sequence within these *Anopheles* genes, for example, the target sequences within the identified genes may include, but are not limited to, the sequences found in Table 4 and Table 6, including, for example, AGAP008903: ATTGGTTCATCGAGCGTGAACGCAA (SEQ ID NO:23), AGAP008903:CCAGCACCAGCCAACGAGGAACACT (SEQ ID NO:24), AGAP003014:AGCTGAACGACAACCTGCTGCTCGG (SEQ ID NO:25), AGAP011489:GCTCGGTACGGTACAGTTTCACTGC (SEQ ID NO:26). AGAP007987:GCTCCATTCGGATCAATCACACATC (SEQ ID NO:27), AGAP007596: GCAGAACGGACAAGAGACAGAAGAT (SEQ ID NO:28), AGAP007596:ATGAACAGTATTTCGCTGAAGGAGA (SEQ ID NO:29), AGAP007254: GCAAGAGAAAGGATCGAAATCGATG (SEQ ID NO:30), AGAP009777:GTGCTGGATAGAATTGCATTTAAAT (SEQ ID NO:31), AGAP011133:GTACCAATTGCATTCGATAGAAGCA (SEQ ID NO:32), AGAP011133: CGTTCAATTTCTTGTGGCAAATGTG (SEQ ID NO:33), AGAP010510:CGACGAGTTCGAACAGGAAGACTGC (SEQ ID NO:34), AGAP010510:CCTACAAATACCTATGGATAGGAAT (SEQ ID NO:35), AGAP010510: ACAGCAGCTACTTCGTCGAGTGGA (SEQ ID NO:36), AGAP004548:GGAATGACTAGAATGGGAATTACTG (SEQ ID NO:37), AGAP004548: GCAAGAGAAAGGATCGAAATCGATG (SEQ ID NO:38), AGAP010265:GCGAGACGATCAATTTGGTCACTAC (SEQ ID NO:39), AGAP008903:GTAGGATTATGAACTCGCAAGATCA (SEQ ID NO:40), AGAP008903: GAACGAGAATCGTTGCAAATAAATA (SEQ ID NO:41), AGAP007987:CCTCCATCTCGATGCTGTATCTGAA (SEQ ID NO:42), AGAP007987: GGTCGACTCTGTCAGTGTACCAAAG (SEQ ID NO:43), AGAP003014:CCACCACTGCCAACAACAACAACAA (SEQ ID NO:44), AGAP003014: GAACCAGAAGGATGACGACTTGAAC (SEQ ID NO:45), AGAP007254: GCAAGAGAAAGGATCGAAATCGATG (SEQ ID NO:46), AGAP007254: GCAAGAGAAAGGATCGAAATCGATG (SEQ ID NO:47), AGAP000891:CCAACTGCATCGACTGTCTGGACCG (SEQ ID NO:48), AGAP000891:ATAGTACCGTGGACAGCAAGGAGCG (SEQ ID NO:49), AGAP011489:CGGTACAGTTTCACTGCGTGGCGAC (SEQ ID NO:50), AGAP003014: GGTGGACTATTACGGGCAACTTTGG (SEQ ID NO:51), AGAP003014:GTGGTGGACTATTACGGGCAACTTT (SEQ ID NO:52), AGAP008903:CATCGAGCGTGAACGCAAACTTGCA (SEQ ID NO:53), AGAP009978:

GAAGAAGGATGTTACGAATGTGCTA (SEQ ID NO:54), AGAP009978:GGAAGATGTT-TAATATCGTCGACAA (SEQ ID NO:55), AGAP009978: GGGAGTGGTTGCATGCGAATCACAA (SEQ ID NO:56), AGAP009978:CGAT-GAGCAAGTAAACGAACTGATC (SEQ ID NO:57) and combinations thereof.

It is predicted, and would be understood by the skilled person, that also orthologs of these target genes represent further targets for down-regulation in the control of other insect and/or arachnid species. Thus, arthropod orthologs of the nucleic acid molecules of the present invention are also contemplated.

Protein or nucleotide sequences are likely to be homologous if they show a "significant" level of sequence similarity or identity. Truly homologous sequences are related by divergence from a common ancestor gene. Sequence homologs can be of two types: (i) where homologs exist in different species they are known as orthologs, e.g. the α-globin genes in mouse and human are orthologs, (ii) paralogs are homologous genes within a single species, e.g. the α- and β-globin genes in mouse are paralogs. By "orthologs" is meant herein both types of homologs referred to above.

In one embodiment, the ortholog will share at least about 40%, 50%>or 60%>nucleotide-sequence identity with the nucleotide sequence of the genes as set forth in any one of Tables 1, 3, 5 or 6 (e.g. SEQ ID Nos: 58-217 and 247-275). Preferably, the ortholog will share at least about 70%, 75%, 80%>, 85%>, 90%, more preferably at least about 95% and even more preferably at least about 96%, 97%, 98% or 99% sequence identity with the nucleotide sequence as set forth in any one of Tables 1, 3, 5 or 6 (.e.g. SEQ ID NOs 58-217 and 247-275). Orthologs of the genes described herein can be found at vectorbase.org and are incorporated by reference in their entirety.

According to another embodiment, the invention encompasses target genes which are arthropod orthologs of a gene comprising, consisting essentially of, or consisting of a nucleotide sequence as represented in any of Tables 1, 3 or 5 (e.g. SEQ ID NOs 58-217 and 247-275). By way of example, ortholog may comprise a nucleotide sequence as represented in any of SEQ ID NOs 58-217 and 247-275, or a fragment thereof. In some embodiments, the orthologous sequence may correspond to the specific target sequences identified within the target genes, for example, orthologous sequences to any one of the target sequences listed in Tables 2, 4 or 6 (e.g. SEQ ID NOs: 1-57 and 218-275). In some cases, the sequences targeted by a synthetic siRNA to *Aedes* and *Anopheles* orthologous genes, for example, but not limited to, the genes listed in Table 6 may be perfectly conserved between the different mosquito species. In other cases, the two orthologous genes in *A. aegypti* and *A. gambiae* may both be required for survival and targeted by two different siRNA target sequences which are not perfectly conserved between the two genes or in other species bearing the same orthologous genes.

Suitably, the sequences and genes targeted by the present technology are specific to mosquitoes. Down-regulation or inhibition of target gene expression is "specific" when down-regulation or inhibition of the target gene occurs without resulting in any detrimental effects on other genes of the targeted organism or genes of other non-related organisms (e.g., humans, mammals, etc.). The targeted sequences selected were analyzed and determined to have little risk for targeting genes in humans. Methods of determining if sequences specifically target human genes are known in the art, and include, for example, assessing human risk empirically through toxicity testing on human cells in vitro and on animal models in vivo, and in silico methods to select only risk-reduced sequences for siRNA synthesis, as described in the Examples below.

The iRNA of the present technology may be a small interfering RNA (siRNA), a short hairpin RNA (shRNA), double stranded RNA (dsRNA) or RNA construct. In some embodiments, the shRNA is encoded in a DNA construct or vector which allows for expression of the iRNA within a target cell.

Some embodiments of the present disclosure provide a DNA construct encoding the iRNA, wherein the DNA construct is able to express the iRNA. Suitable DNA constructs will depend on the type of cell in which to express the RNA. In some embodiments, the DNA construct is a linear or a closed circular plasmid or expression vector. In some embodiments, the DNA constructs will be integrated into the host cell genome, for example, integrated in to a yeast or bacterial cell genome.

In some embodiment, the DNA construct is a suitable expression vector. Sequences that encode the iRNA of the present technology can be inserted into a vector under the control of a suitable promoter that functions in one or more microbial hosts to drive expression of a linked coding sequence or other DNA sequence. Suitable vectors are known in the art and selecting the appropriate vector will depend on the size of the nucleic acid to be inserted into the vector and the particular host cell to be transformed with the vector. Vectors may include one, but are not limited to, one or more of the following: a signal sequence, an origin of replication, one or more selectable marker genes, terminators, enhancers and/or a constitutive or inducible promoter allowing expression of exogenous DNA. Vectors can also include viral vectors and the like.

In some embodiments, the iRNA is produced by a host cell which can express the iRNA from a DNA construct or expression vector. Suitable cells, include, but are not limited to, a bacterial, algal or yeast cell engineered to produce or express the iRNA from the DNA construct. Other suitable host cells, e.g., microorganism cells or plant cells, are known in the art. In some embodiments, the host cell expresses at least two iRNA, alternatively at least three iRNA, alternatively at least four iRNA. In some embodiments, the host cell expresses from 1-10 iRNA.

In some embodiment, the host cell may be stably transformed to express at least one iRNA of interest. In further embodiments, the host cell may be stably transformed to express at least two iRNA, alternatively at least three iRNA, alternatively at least four iRNA, alternatively at least five iRNA. Suitable DNA constructs or vectors to express multiple iRNA from multiple sequences are known in the art. In some embodiments, the host cell may stably express from about 1-10 iRNA, suitably about 1-5 iRNA.

Stable transformants may be produced by incorporating the sequence of the iRNA into the host cell genome. Methods of forming stable transformants of host cells are known in the art.

In order to avoid introducing the replicating host cells or live microorganisms into the environment, host cells may be killed or inactivated (e.g. unable to grow and/or replicate) before being incorporated into the compositions of the present invention. Host cells are preferably killed or inactivated in a manner that maintains the ability of the host cell to act as a larvicide (i.e., the inactivation does not disrupt the iRNAs contained within said host cell). In some embodiments, the siRNA can be purified from the host cell before incorporating into the compositions. Suitable methods of killing or inactivating the host cell are known in the art, and include, but are not limited to, heat-inactivation, high pressure, plasma treatment at atmospheric pressure, sonication, low-amperage electric treatment, or dense phase carbon dioxide processing.

In some embodiments, the present invention provides a bacterial cell expressing the at least one iRNA described herein. Suitable bacterial cells are known in the art and include, but are not limited to, *E. coli, Bacillus thuringiensis israelensis, Lactobacillus* among others.

In some embodiments, the present invention provides a yeast cell expressing the at least one iRNA as described herein. Suitable strains of yeast are known in the art, and include, but are not limited to, *Saccharomyces cerevisiae* (baker's yeast), *Saccharomyces boulardii, Pichia pastoris*, among others. Yeast is an attractive food source for mosquito larvae, which makes it well-suited as a delivery system. Other advantages of yeast include relatively low cost of production, the capacity to produce interfering RNA through yeast cultivation, and the ability to pack and ship dried yeast in shelf-stable forms. Concerns about introducing live organisms into treated sites can be ameliorated by using heat-killed yeast, which retain larvicidal potency.

In one embodiment, the yeast cell is *Saccharomyces cerevisiae. S. cerevisiae* is a model organism that is genetically tractable and inexpensive to culture and can be engineered to produce interfering RNA in the form of short hairpin RNA (shRNA), which can be easily amplified through yeast cultivation. Yeast is both a strong odorant attractant and a source of nutrition for laboratory-bred *A. aegypti* larvae (Mysore et al., 2013). Moreover, dried yeast, a granulated form in which yeast is commercially sold, can be packaged and shipped, making it ideal for delivery to countries with extant *A. aegypti* populations and endemic virus transmission.

The present shRNA produced and delivered in *S. cerevisiae* can be utilized as targeted and efficient mosquito larvicidal agent.

In some embodiments, the host cell expresses at least two iRNA that target a single gene, alternatively at least three iRNA that target a single gene, alternatively at least four RNA that target a single gene. In another embodiment, the host cell expresses at least two iRNA that target two different genes, alternatively at least three iRNA that target at least two different genes, alternatively at least three iRNA that target at least two different genes, alternatively at least three different iRNA that target at least two different genes.

In one embodiment, a host cell, e.g. a yeast cell expresses at least two iRNA that target a single gene. In one embodiment, a host cell expresses at least three iRNA that target a single gene. In one embodiment, a host cell expresses at least three iRNA that target a single gene. In one embodiment, a host cell expresses at least four iRNA that target a single gene.

In one embodiment, a host cell expresses at least two iRNA targeting at least two different genes required for maturation from larva to adult of at least one insect, preferably a mosquito.

In another embodiment, a host cell expresses at least two iRNA targeting at least one gene required for adult insect survival, alternatively at least three iRNA targeting at least one gene required for adult insect survival, alternatively at least four iRNA targeting at least one gene required for adult insect survival, alternatively at least five iRNA targeting at least one gene required for adult insect survival, alternatively at least two iRNA targeting at least two different genes required for adult insect survival, alternatively at least three iRNA targeting at least two different genes required for adult insect survival, alternatively at least four iRNA targeting at least two different genes required for adult insect survival, etc. In a preferred embodiment, the insect is a mosquito.

In another embodiment, a host cell expresses at least three iRINA targeting at least two different genes, alternatively at least four iRNA targeting at least two different genes, alternatively at least five iRNA targeting at least two different genes, alternatively at least three iRNA targeting at least three different genes, alternatively at least four iRNA targeting at least three different genes, alternatively at least five iRNA targeting at least three different genes, alternatively at least six different iRNA targeting at least three different genes, etc. In some preferred embodiments, the host cell is a yeast cell or bacterial cell. In some embodiment, multiple iRNAs may target at least one, at least two, at least three, at least four, at least five different genes required for maturation or development from larva to adult of at least one insect and/or adult insect survival, wherein the insect is preferably a mosquito, alternatively at least two or more insects, preferably two or more mosquito species.

In one embodiment, a host cell, e.g. yeast cell is provided that expresses at least four iRNA, wherein the at least four iRNA target a single gene required for maturation from larva to adult of at least one insect, preferably a mosquito. In another embodiment, the host cell, e.g., a yeast cell, expresses at least four iRNA, wherein the at least four iRNA target at least two different genes required for maturation from larva to adult of at least one insect, preferably a mosquito. In some embodiments, the target gene may also be required for adult insect survival.

Suitably, more than one iRNA may either be expressed by a single DNA construct, or may be expressed by multiple DNA constructs that are introduced into the host cell. In some embodiments, the DNA construct comprises multiple expression sites, each site able to drive the expression of a different nucleotide sequence. By this method, multiple iRNAs can be expressed in a single cell, where the multiple iRNA can either targeting multiple sites on a single gene or target multiple genes within at least one insect, preferably at least one mosquito species.

In one suitable embodiment, a yeast cell expresses at least four iRNA by four different expression sites on a DNA construct or vector. In a preferred embodiment the four iRNA are expressed in the yeast *Saccharomyces cerevisiae.*

Suitable, the yeast may be heat inactivated before contacting the larva. In some embodiments, it is preferred that the yeast is heat inactivated to reduce or eliminate the ability of the yeast to grow once released into a treatment area.

In some embodiments, the yeast is being synthesized into a ready-to use dry formulation.

The present invention also provides a mosquito insecticide composition for preventing and/or controlling mosquito infestations. The compositions may comprise at least one interfering RNA of the present disclosure or at least one host cell expressing at least one interfering RNA of the present disclosure and at least one suitable carrier, excipient or diluents. In some embodiments, the at least one host cell is at least one yeast cell or at least one bacterial cell that expresses at least one iRNA. In some embodiments, the mosquito insecticide is a mosquito larvicide.

In a preferred embodiment, the composition comprises at least one yeast cell comprising at least one iRNA. In some embodiments, the yeast cell is inactivated or killed but maintains its larvicidal properties. In a suitable embodiment, the yeast cell is heat inactivated. In other embodiments, the yeast is inactive by methods known in the art, for example, by high pressure, plasma treatment at atmospheric pressure, sonication, low-amperage electric treatment, or dense phase carbon dioxide processing.

Some compositions may comprise one or more iRNA, for example, at least two iRNA, alternatively at least three iRNA, alternatively at least four iRNA, alternatively at least five iRNA, alternatively at least six iRNA, alternatively at least seven iRNA, alternatively at least eight iRNA, etc. In some embodiments, the compositions comprise from 1-10 different iRNAs. In a suitable embodiment, the composition comprises about 1-5 different iRNAs.

In some embodiments, the compositions comprise a host cell comprising, containing or expressing at least one iRNA described herein.

In some embodiments, the compositions comprise multiple iRNAs that target a single gene required for larval maturation or growth, and, in some embodiments, required for adult insect survival. In some embodiments, the compositions comprise multiple iRNAs that target multiple genes required for mosquito larval maturation or growth, for example, at least two genes, at least three genes, at least four genes, etc.

Methods of delivery iRNA of the present technology include, but are not limited to, e.g. larval soaking, nanoparticles (e.g. Chitosan nanoparticles), bacterial cells, yeast cells, algal cells, ovitraps, dried tablets, sugar feeding, and topical applications among others. Other suitable methods of delivery are known in the art. Thus, compositions may include the necessary components to deliver the iRNA to the larva. For example, compositions may comprise nanoparticles, bacterial cells, yeast cells, algal cells and the like that contain or express the iRNA.

In some instances, the insecticide composition is placed in water. In other instances, the insecticide composition is placed in ovitraps. These are water-filled traps that are treated with the larvicides. They are designed to attract *Aedes* mosquitoes to lay their eggs in larvicide-treated water.

The term “preventing” or “controlling” mosquito infestation comprises the reduction or inhibition of the maturation of mosquito larvae into adults and/or death or decreased survival of adult mosquitoes. Suitable, the reduction or inhibition is measured by a reduction in the number of adult mosquitoes within an area.

Suitable carriers, excipients and diluents are known in the art and include, but are not limited to, for example, water, saline, phosphate buffer saline, and the like. Suitably, the carrier is formulated to the composition depending on the delivery method, for example, spray, powder, pellet, etc.

Figure 7:
FIG. 7 is a picture showing a dried inactivated yeast tablet comprising yeast expressing the synthetic shRNA of the present invention. This tablet is a ready to use mosquito lure that can be placed in the field or water to treat a mosquito infestation.

The compositions may be formulated into suitable forms for treatment of a mosquito infested area. For example, the composition may be in the form of a spray, powder, pellet, gel, capsule, food product or the like. Suitable, the composition comprises inactive yeast cells expressing at least one iRNA. In one embodiment, the composition is a dried inactive yeast pellet, as shown in FIG. 7, containing the synthetic interfering RNA in a tablet. These tablets are ready-to-use lure.

The disclosure further provides methods for controlling, reducing or treating a mosquito infestation comprising exposing at least one mosquito larvae to the at least one interfering ribonucleic acid (iRNA) or a composition described herein in an effective amount to control, reduce or treat the mosquito infestation. The mosquito infestation may be controlled, reduced or treated by inhibiting the larvae from maturing into adult mosquitoes by inhibiting at least one gene require for larval maturation or by decreasing the survival of adult mosquitoes. Suitable, inhibition of maturation may include the reduction in the number of adult mosquitoes found within a given area.

The disclosure further provides methods for controlling, reducing or treating a mosquito infestation comprising exposing at least one mosquito larvae or adult to the at least one interfering ribonucleic acid (iRNA) or a composition described herein in an effective amount to control, reduce or treat the mosquito infestation. The mosquito infestation may be controlled, reduced or treated by inhibiting the larvae from maturing into adult mosquitoes or by killing or decreasing survival of an adult mosquito.

Mosquito infestations refers to a population of at least one species of mosquito within a given area, for example, a population of one or more of the following mosquito species described herein. In some embodiments, the population comprises at least two mosquito species, alternatively at least three mosquito species, alternatively at least four mosquito species and can range depending on location. In some embodiments, the population comprises from about 1-20 mosquito species, alternatively from 1-10.

The present disclosure provides suitable insecticides comprising at least one iRNA which specifically targets and suppresses expression of one target gene, e.g. a larva maturation gene or adult survival gene within an insect, preferably a mosquito.

The term insecticide is used to describe a composition or iRNA which is able to target and kill an insect at any stage of its life cycle. For example, the insecticide may target and kill the insect at the larval stage or as a mature adult insect. In some instances, the insecticide is a larvicide.

The term larvicide is used to describe a composition or iRNA which specifically down-regulates or suppresses a gene required for the maturation, development or survival of the larval stage of development. In other words, a larvicide kills larva or inhibits larva from maturing into the pupa and/or adult stage of development, resulting in a reduction in the number of larva that develop into adults. In some instances, the larvicide may additionally be able to inhibit or reduce survival of adult mosquitoes resulting in adult mosquito death.

The mechanisms by which to deliver the iRNA of the present invention allow for the simultaneous delivery of multiple insecticides. This reduces the likelihood of developing insecticide resistant strains arising from point mutations in any one target sequence and also facilitates the development of broader based insecticides targeting multiple arthropod pests.

It should be apparent to those skilled in the art that many additional modifications beside those already described are possible without departing from the inventive concepts. In interpreting this disclosure, all terms should be interpreted in the broadest possible manner consistent with the context. Variations of the term “comprising” should be interpreted as referring to elements, components, or steps in a non-exclusive manner, so the referenced elements, components, or steps may be combined with other elements, components, or steps that are not expressly referenced. Embodiments referenced as “comprising” certain elements are also contemplated as “consisting essentially of” and “consisting of” those elements. The term “consisting essentially of” and “consisting of” should be interpreted in line with the MPEP and relevant Federal Circuit's interpretation. The transitional phrase “consisting essentially of” limits the scope of a claim to the specified materials or steps “and those that do not materially affect the basic and novel characteristic(s)” of the claimed invention. “Consisting of” is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The invention will be more fully understood upon consideration of the following non-limiting examples.

Example 1: Screening for Larva-Lethal siRNA

This example demonstrates the development of a new class of insecticides for control of disease vector mosquitoes using short-length interfering RNA as mosquito specific larvicides.

RNA interference (RNAi) has been used for functional genetic studies in a wide variety of organisms, including insects (Yu et al., 2013; Zhang et al., 2013). The RNAi pathway is initiated by Dicer, which cleaves long double stranded RNA (dsRNA) into short 20-25 nucleotide-long small interfering RNAs (siRNAs) that function as sequence-specific interfering RNA. siRNAs silence genes that are complementary in sequence by promoting transcript turnover, cleavage, and disruption of translation (Zhang et al., 2013).

Numerous studies have demonstrated that target gene silencing through RNAi can promote insect death (reviewed by Li et al., 2012). For example, Baum et al. (2007) engineered transgenic corn plants expressing dsRNA targeting the western corn rootworm *Diabrotica virgifera virgifera* LeConte. dsRNA insecticidal corn targeting this species was recently registered by the U.S. Environmental Protection Agency (EPA, 2015b), which deemed that this intervention meets the regulatory standards described in the Federal Insecticide, Fungicide, and Rodenticide Act (FIRFA, 2015). Likewise, Whyard et al. (2009) showed that *Tribolium castaneum, Acyrthosiphon pisum*, and *Manduca sexta* were selectively killed when fed species specific dsRNA targeting vATPase. These and other studies suggest that RNAi can be exploited to control insect agricultural pests.

Our recent studies have demonstrated that synthetic siRNA, which can be designed to be species-specific, can selectively target *A. aegypti* larval genes (Mysore et al., 2013, 2014a,b, 2015). We performed a high throughput large-scale siRNA screen to identify genes required for mosquito survival. Genes required for larval survival were identified in *A. aegypti* and *Anopheles coluzzii*, both of which are straightforward to rear under laboratory conditions and appropriate selections for large-scale screening studies. For each larval lethal gene, we identified sequences that are conserved in multiple anopheline and aedine vector mosquito species. 2-3 interfering RNA target sequences corresponding to each larval lethal gene are identified. This will combat pesticide resistance arising from a point mutation in any one target sequence.

Larvicide Screen in *A. aegypti*

The Scheel laboratory at the Indiana University School of Medicine, South Bend, Ind., USA, in collaboration with the David W. Severson laboratory (University of Notre Dame, Notre Dame, Ind., USA) has screened hundreds of siRNAs for mosquito larval lethality. Custom siRNAs corresponding to putative larval lethal genes were purchased from Integrated DNA Technologies (IDT, Coralville, Iowa) and are being used in larvicide trials that are being conducted in the laboratory per the WHO (2005) guidelines. For the screen, siRNAs are delivered to mosquito larvae through microinjection (Clemons et al., 2010) and through larval soaking (Singh et al., 2013). Two or more biological replicate experiments with 20-30 age-synchronized larvae were performed, and larval lethality assessed at the end of the fourth instar. siRNAs that generate significant mortality as compared to treatment with control siRNA (which lacks significant sequence homology to *A. aegypti* and *A. gambiae* genes) are selected for further bioactivity characterization.

~5,000 *D. melanogaster* genes (*drosophila*) are larval lethals (St. Pierre et al., 2014), meaning that loss of function mutations in these genes result in larval death. *A. aegypti* orthologs for most of these genes have been identified (Kasprzyk et al., 2011; Megy et al., 2012), and ~2,500 are expressed in all four *A. aegypti* larval instars (Akbari et al., 2013). Sequences of these *A. aegypti* orthologs downloaded from Vectorbase (Megy et al., 2012) were imported into the Integrated DNA Technologies (IDT) siRNA design tool program, allowing for identification of siRNA duplexes corresponding to each putative *A. aegypti* larval lethal gene. Custom IDT screening dsRNA oligos were used to perform a larval lethal screen in *A. aegypti*. Neural genes, a focus of the Scheel laboratory, as well as *A. aegypti* orthologs of *Drosophila* larval lethal genes that were also identified as larval lethals in a recent *Tribolium castaneum* study (Schmitt-Engel et al., 2015) are among the genes prioritized in the *A. aegypti* screen to date. The screen was initially conducted using chitosan nanoparticles as described (Zhang et al., 2015). Although this procedure worked well (AAEL007292 and AAEL007548 in Table 1 were initially identified in this manner). Later screening used siRNAs through microinjection, which given the technical expertise of our staff who routinely inject developing mosquitoes, was still relatively high-throughput and required less siRNA per trial.

For these experiments, siRNAs were microinjected into each of 30 third instar larvae as described (Clemons et al., 2010; Blitzer et al., 2005); ~10 pmol siRNA were injected in a 30 nL volume per larva. Simultaneously, we also began screening the same siRNAs through delivery via the larval soaking method described by Whyard et al. (2009). For soaking experiments, 20 larvae were exposed to 20 ul of 0.5 ug/ul siRNA for four hours (rather than daily as indicated by Whyard et al., 2009) allowing for detection of siRNAs that were capable of killing mosquitoes following only a brief exposure period, which may better simulate the field. First instar larvae, which are technically difficult to microinject, were used in the soaking experiments. Third instar larvae, which due to their large size require a larger (and therefore more expensive) volume of siRNA treatment solution in soaking experiments, were used in the microinjection experiments. Following siRNA delivery via nanoparticles, soaking, or through microinjection, larvae were reared and lethality evaluated as discussed in the standardized WHO (2005) larvicide testing guidelines.

siRNAs corresponding to target sequences in >400 putative larval lethal genes have been tested to date. ~30% (~100) of these siRNAs resulted in significant larval death following microinjection or soaking experiments ($p<0.05$ in paired t-test). siRNAs targeting 10 of these genes induced an average mortality rate greater than or equal to 50% following microinjection (Table 1, two or more replicate experiments were performed). These same siRNAs also generated significant death ($p<0.05$) following brief four hour soaking of first instar larvae. These 10 genes, which were demonstrated to be larval lethals when targeted beginning in either the first (soaking) or third (microinjection) instar, and for which targeting resulted in death after a brief four hour exposure to siRNA, have been selected for further evaluation in our yeast interfering RNA project.

TABLE 1

Top hits identified in larval lethal screen in *A. aegypti*. Gene functions and the average percentage larval mortality (from two or more biological replicate experiments) observed following siRNA injection are indicated.

| Gene ID | Accession No. | SEQ ID NO: (nucleotide) | Function | Average Larval Mortality |
|---|---|---|---|---|
| AAEL007292 | XM_001652616 | 58 | Unc-76 kinesin binding | 50% |
| AAEL007548 | XM_001658387 | 59 | Leukocyte receptor cluster (lrc) member | 65% |
| AAEL007546 | XM_001658390 | 60 | Actin-related protein 2/3 complex subunit 1A | 65% |
| AAEL007563 | XM_001658402 | 61 | Dual oxidase | 55% |
| AAEL007876 | XM_001652912 | 62 | Tyrosine-protein kinase | 50% |
| AAEL009273 | XM_001653725 | 63 | Inosine-5'-monophosphate dehydrogenase | 60% |
| AAEL007718 | XM_001652797 | 64 | eIF3b | 50% |
| AAEL004756 | XM_001649686 | 65 | Vesicle docking protein | 80% |
| AAEL003517 | XM_001656855 | 66 | Ubiquitin carboxyl-terminal hydrolase | 60% |
| AAEL014566 | XM_001647781 | 67 | Wnt-5 signaling protein | 55% |
| AAEL007298 | XM_001652617<br>XM_001652618 | 68 | Unknown | >50% |
| AAEL007554 | XM_001658382 | 69 | Methylosome protein | >50% |
| AAEL000032 | XM_001647881<br>XM_001647880<br>XM_001647882 | 70 | 40S ribosomal protein S6 | >50% |
| AAEL004874 | XM_001649902 | 71 | LIM domain containing protein | >50% |

All genes can be found at ncbi.nlm.nih.gov/nuccore by searching the accession number or at vectorbase.org by searching their name or accession number.

TABLE 2

25 bp nucleotide sequences that can target and downregulate larval lethal genes for at least *A. aegypti*.

| 25 nucleotide target sequence | SEQ ID NO: | Gene Name Targeted |
|---|---|---|
| CTAGCATCATCTTCCGACCGAACCA | 1 | AAEL007292 |
| GCACAAGTGGCATTGATAATCCTAT | 2 | AAEL007298 |
| GTATCAGTCAGTATCAGAACCAGAA | 3 | AAEL007548 |
| CGCTGGTTCTGCTGAGAATCAACCG | 4 | AAEL007546 |
| GGGAGAACAGCGACAGCAAGGAGAA | 5 | AAEL007554 |
| GAACGACAATGCTGTATATTTGCGA | 6 | AAEL007563 |
| CCACAAGCTGCGTCACTTCTACGAC | 7 | AAEL000032 |
| CGAGGAGCTGAATGAGATTAAACCG | 8 | AAEL007876 |
| CGATGAGTCTGAAGAGATACGAATC | 9 | AAEL009273 |
| CCTCCAGGCTGGATCGTTTGAGTTT | 10 | AAEL007718 |
| CGATGATGTCGGATGGGATGTCCAG | 11 | AAEL004874 |
| GAAGAAGTACCGTGTGGAAGTGGGA | 12 | AAEL004756 |
| CACTGACAATGATCCGATAAAGACA | 13 | AAEL007292 |
| GTACCTAGTCGATGGTCAATCAGAG | 14 | AAEL007554 |

TABLE 2-continued 25 bp nucleotide sequences that can target and downregulate larval lethal genes for at least *A. aegypti*.

| 25 nucleotide target sequence | SEQ ID NO: | Gene Name Targeted |
|---|---|---|
| CATTGTTATTACTCACGATGTCAAG | 15 | AAEL007563 |
| GGAGAAGTGATGACCGTCATGAGAA | 16 | AAEL007563 |
| GGACGTCATTGAAACGGATTTGCTA | 17 | AAEL007563 |
| GGAACTGCTAACCGATCAAGAGAAC | 18 | AAEL004756 |
| CGTTATTACCATTACGGTAAATGGC | 19 | AAEL004756 |
| GGGAGGTGATAAGAAACGATGCTCT | 20 | AAEL004756 |
| GCAAGACAGATTTCGATAAAGATCA | 21 | AAEL007548 |

At this juncture, interfering RNAs corresponding to the genes AAEL007292, AAEL007548, and AAEL004756 are our most promising *A. aegypti* larvicides. The sequences initially targeted in these genes are:

(SEQ ID NO: 1)
AAEL007292: CTAGCATCATCTTCCGACCGAACCA (SEQ ID NO: 3)
AAEL007548: GTATCAGTCAGTATCAGAACCAGAA (SEQ ID NO: 12)
AAEL004756: GAAGAAGTACCGTGTGGAAGTGGGA

All of these target sequences are well conserved in *Aedes albopictus* (88-92% identity), which also vectors Zika and dengue viruses. Our initial computational evaluations of siRNA targeting these sequences suggest that they have little potential for targeting genes in humans.

Determining Potential of iRNA for Targeting Genes in Human

Multiple in silico methods to select only risk-reduced sequences for siRNA synthesis are used to minimize potential for targeting of human genes. Prior to synthesis, the initial set of designs generated with Integrated DNA Technologies (IDT) Custom DsiRNA Design Tool (IDT 2016) is first restricted to those with i-Scores greater than 60 (which correlates with a greater than 75% likelihood of effective functionality) (Ichihara et al. 2007). In mammalian cells, siRNAs can exert off-target effects through two distinct mechanisms (Doench et al. 2003); reducing the risk of off-targeting via both of these mechanisms inform both pre-synthesis design and an additional round of scrutiny after initial laboratory testing for effective inhibitory functionality. The seed-dependent off-targeting pathway requires matching of the six nucleotide siRNA seed region of nucleotides in position 2 to position 7 to the 3' untranslated region of the transcript. Risk-reduction is associated with a lower number of times a given six-nucleotide sequence is represented in the 3' UTR of the human transcriptome; the number of occurrences of a given hexamer is called the seed complement frequency (SCF) (Anderson et al. 2008). To achieve risk-reduced design with respect to the seed-dependent pathway, SCF in the mid-high and high ranges, as defined in Anderson et al. 2008, are disallowed, favoring designs with SCF in the low range. The range between the lowest and highest SCF designs may be 10-fold or greater, which can correspond to a greater than 3-fold difference in undesired off-target inhibitory action without significant difference in desired target inhibition. To address the overall complementarity-dependent off-targeting pathway, this limited subset is then further restricted to those with at least four mismatches over nineteen nucleotide sequences; this standard is more stringent than published threshold for target-specificity of two-mismatches (Naito et al. 2009).

The risk of off-target effects though the overall complementarity is extended to non-human species through Basic Local Alignment Search Tool (BLAST) searches, including broad general categories such as birds and plants, pollinating insects, and specific organisms present in the geographic region of intended use, with mosquito predators as a prioritized class. As an additional pre-synthesis safeguard, the IDT Custom DsiRNA Design Tool (IDT 2016) can, as of February 2016, be configured to report and specify cross-reacting transcripts; designs with no cross-reacting transcripts reported are selected for synthesis. A motif of UGUGU has been found to stimulate the innate immune responses in mammalian organisms and human cells (Judge et al. 2005); the presence of this immunostimulatory motif disqualifies a design from selection for synthesis. Additional in silico criteria can assist with candidate selection among synthesized designs which have demonstrated the highest efficacy as mosquito larvicides in laboratory testing. Among these considerations are thermodynamic stability of the extended seed region of nucleotides in positions 2-8, with a benchmark $T_m$ of 21.5° C. (Ui-Tei et al. 2008) and high average guanine or cytosine content in positions 8-15 (Kamola et al. 2015). Additional nucleotide-by-nucleotide analysis of pairwise BLAST alignments can be guided utilizing the results of finely detailed studies (Wee et al. 2012, Kamola et al. 2015). All of these elements, not found in combination in any single algorithm or tool, together dramatically reduce potential risk to off-target organisms, including and especially humans, before any exposures occur beyond the protections of the laboratory.

Larvicide Screen in Anopheline Mosquitoes

We applied the results of our *A. aegypti* screen to identify larval lethal genes in anopheline mosquitoes. As in *A. aegypti*, genes that were demonstrated to be larval lethals when targeted in either the first (soaking delivery) or third (microinjection delivery) instar, and for which targeting resulted in death after a brief four hour exposure to siRNA, have been selected for further evaluation. At this juncture, these genes have been identified from *Anopheles coluzzii*, and all of these target sites are preserved in the malaria vector *Anopheles gambiae*.

TABLE 3 provides a list of the larval lethal genes targeted in *Anopheles*. Top hits identified as larval lethal genes identified in *Anopheles*.

| Gene | Accession No. | SEQ ID NO: | Function |
|---|---|---|---|
| AGAP000891 | XM_316868 | 72 | Phosphatidylinositide phosphatase |
| AGAP008903 | XM_001689147 | 73 | Unknown |
| AGAP003014 | XM_311865 | 74 | fasciculation and elongation protein zeta 2 |
| AGAP011489 | XM_317813 | 75 | Protein tyrosine kinase |
| AGAP007987 | XM_317480 | 76 | bone morphogenetic protein |
| AGAP007596 | XM_308277 | 77 | Septin |
| AGAP007254 | XM_308548 | 78 | ribosome biogenesis protein UTP30 |
| AGAP009777 | XM_318870 | 79 | mothers against decapentaplegic homolog |
| AGAP011133 | XM_309514 | 80 | Inosine-5'-monophosphate dehydrogenase |
| AGAP010510 | XM_558416 | 81 | tubulin beta |
| AGAP004548 | XM_001237547 | 82 | LIM domain-containing protein |
| AGAP010265 | XM_319454 | 83 | Delta signaling protein |
| AGAP009978 | XM_319115 | 84 | dual oxidase: peroxidase and NADPH-oxidase domains |

All genes can be found at ncbi.nlm.nih.gov/nuccore by searching the accession number or at vectorbase.org by searching their name or accession number.

TABLE 4 siRNA targeted sequences corresponding to the larval lethal screen in anopheline mosquitoes that result in at least 50% lethality.

| 25 nucleotide sequence | SEQ ID NO: | Gene Name Targeted |
|---|---|---|
| CCAACTGCATCGACTGTCTGGACCG | 22 | AGAP000891 |
| ATTGGTTCATCGAGCGTGAACGCAA | 23 | AGAP008903 |
| CCAGCACCAGCCAACGAGGAACACT | 24 | AGAP008903 |
| AGCTGAACGACAACCTGCTGCTCGG | 25 | AGAP003014 |
| GCTCGGTACGGTACAGTTTCACTGC | 26 | AGAP011489 |
| GCTCCATTCGGATCAATCACACATC | 27 | AGAP007987 |
| GCAGAACGGACAAGAGACAGAAGAT | 28 | AGAP007596 |
| ATGAACAGTATTTCGCTGAAGGAGA | 29 | AGAP007596 |
| GCAAGAGAAAGGATCGAAATCGATG | 30 | AGAP007254 |
| GTGCTGGATAGAATTGCATTTAAAT | 31 | AGAP009777 |
| GTACCAATTGCATTCGATAGAAGCA | 32 | AGAP011133 |
| CGTTCAATTTCTTGTGGCAAATGTG | 33 | AGAP011133 |
| CGACGAGTTCGAACAGGAAGACTGC | 34 | AGAP010510 |
| CCTACAAATACCTATGGATAGGAAT | 35 | AGAP010510 |
| ACAGCAGCTACTTCGTCGAGTGGA | 36 | AGAP010510 |
| GGAATGACTAGAATGGGAATTACTG | 37 | AGAP004548 |
| GCAAGAGAAAGGATCGAAATCGATG | 38 | AGAP004548 |
| GCGAGACGATCAATTTGGTCACTAC | 39 | AGAP010265 |
| GTAGGATTATGAACTCGCAAGATCA | 40 | AGAP008903 |
| GAACGAGAATCGTTGCAAATAAATA | 41 | AGAP008903 |
| CCTCCATCTCGATGCTGTATCTGAA | 42 | AGAP007987 |
| GGTCGACTCTGTCAGTGTACCAAAG | 43 | AGAP007987 |
| CCACCACTGCCAACAACAACAACAA | 44 | AGAP003014 |
| GAACCAGAAGGATGACGACTTGAAC | 45 | AGAP003014 |
| GCAAGAGAAAGGATCGAAATCGATG | 46 | AGAP007254 |
| GCAAGAGAAAGGATCGAAATCGATG | 47 | AGAP007254 |
| CCAACTGCATCGACTGTCTGGACCG | 48 | AGAP000891 |
| ATAGTACCGTGGACAGCAAGGAGCG | 49 | AGAP000891 |
| CGGTACAGTTTCACTGCGTGGCGAC | 50 | AGAP011489 |
| GGTGGACTATTACGGGCAACTTTGG | 51 | AGAP003014 |
| GTGGTGGACTATTACGGGCAACTTT | 52 | AGAP003014 |
| CATCGAGCGTGAACGCAAACTTGCA | 53 | AGAP008903 |
| GAAGAAGGATGTTACGAATGTGCTA | 54 | AGAP009978 |

TABLE 4-continued siRNA targeted sequences corresponding to the larval lethal screen in anopheline mosquitoes that result in at least 50% lethality.

| 25 nucleotide sequence | SEQ ID NO: | Gene Name Targeted |
|---|---|---|
| GGAAGATGTTTAATATCGTCGACAA | 55 | AGAP009978 |
| GGGAGTGGTTGCATGCGAATCACAA | 56 | AGAP009978 |
| CGATGAGCAAGTAAACGAACTGATC | 57 | AGAP009978 |
| GCCTAATCAACCTGATCGACCACAA | 218 | AGAP000891 |
| GGATGCACGAATCTTCGATGATATG | 219 | AGAP000891 |
| GTAGGATTATGAACTCGCAAGATCA | 220 | AGAP008903 |
| CCAGCACCAGCCAACGAGGAACACT | 221 | AGAP008903 |
| CATCGAGCGTGAACGCAAACTTGCA | 222 | AGAP008903 |
| GGTGGACTATTACGGGCAACTTTGG | 223 | AGAP003014 |
| GTGGTGGACTATTACGGGCAACTTT | 224 | AGAP003014 |
| GCAGTGGTCAAATCGTTTTAATAGC | 225 | AGAP010265 |
| CGAATCTTGAAAACGATTACCGCTG | 226 | AGAP010265 |
| ATTACTCCATCAAGAGCGACATCTA | 227 | AGAP011489 |
| GGACAAAGATCTGCAGTATCTGCAT | 228 | AGAP011489 |
| CGGTACAGTTTCACTGCGTGGCGAC | 229 | AGAP011489 |
| CCTCCATCTCGATGCTGTATCTGAA | 230 | AGAP007987 |
| CAGGTGATGGTGTACGACATCGTGC | 231 | AGAP007987 |
| ATCCTAAAACGCTAGTCGAGATAGA | 232 | AGAP007987 |
| ATGAACAGTATTTCGCTGAAGGAGA | 233 | AGAP007596 |
| CAATAACAATCACAACGGTCTGAAC | 234 | AGAP007596 |
| GGTTGAATGTGCAGGCGATCAACCT | 235 | AGAP007254 |
| AGATTAAGGAATCGATTGAGCAGGC | 236 | AGAP007254 |
| GCAGGTAACGGACGAGGAAGATTCA | 237 | AGAP007254 |
| GAAGAAGGATGTTACGAATGTGCTA | 238 | AGAP009978 |
| GGAAGATGTTTAATATCGTCGACAA | 239 | AGAP009978 |
| GGGAGTGGTTGCATGCGAATCACAA | 240 | AGAP009978 |
| CGATGAGCAAGTAAACGAACTGATC | 241 | AGAP009978 |
| GCAGTGGTCAAATCGTTTTAATAGC | 242 | AGAP010265 |
| CGAATCTTGAAAACGATTACCGCTG | 243 | AGAP010265 |
| CATCGAGCGTGAACGCAAACTTGCA | 244 | AGAP008903 |
| CGCTGCAGGAAGCGAACAACATTAT | 245 | AGAP011133 |
| GCTCGATCAGCTATTACGAACTGAA | 246 | AGAP009777 |

siRNAs corresponding to the genes AGAP000891, AGAP008903, and AGAP011489, are promising anopheline larvicides. The sequences initially targeted in these genes are:

(SEQ ID NO: 48)
AGAP000891: CCAACTGCATCGACTGTCTGGACCG (SEQ ID NO: 23)
AGAP008903: ATTGGTTCATCGAGCGTGAACGCAA (SEQ ID NO: 26)
AGAP011489: GCTCGGTACGGTACAGTTTCACTGC

The target sequence in AGAP000891 is perfectly conserved in *A. gambiae, A. merus, A. arabiensis*, and *A. melas*. The AGAP008903 target sequence is found in *A. gambiae, A. funestes, A. sinensis, A. dirus, A. arabiensis, A. quadriannulatus, A. melas*, and *A. christyi*.

The target sequence noted for AGAP011489 is also conserved in *A. quadriannulatus*, and *A. merus*. Our computational evaluations of siRNAs targeting these sequences suggest that they have little potential for targeting genes in humans.

We have identified multiple siRNA target sites in each of our top aedine and anopheline genes. The use of multiple siRNA allows us to combat the potential for pesticide resistance emerging from a point mutation in any one target sequence. For anopheline mosquitoes, we select sequences that are conserved in multiple anopheline species, specifically those that vector malaria parasites in the Bill and Melinda Gates Foundation priority areas, which include sub-Saharan Africa, the Greater Mekong Subregion, and Hispaniola. In this manner, we identified larvicides that can kill multiple malaria vector species across the globe. Likewise, as we identify multiple target sites in each *A. aegypti* larval lethal gene, we can identify sequences conserved between *A. aegypti* and *A. albopictus*, which has a broader distribution within the United States.

Additional genes identified as larval lethal for *Aedes* genus, include the genes listed in Table 5. Suitable iRNA may target any gene listed in Table 5 or an ortholog thereof. All sequences for the genes can be found at vectorbase.org by searching the gene or accession number at ncbi.nlm.nih.gov/nuccore, and are incorporated by reference in their entireties. Orthologs of each gene can also be found at vectorbase.org, which are also incorporated by reference in their entireties.

TABLE 5

Additional larval lethal genes of the *Aedes* genus. All gene sequences can be found at www.vectorbase.org by searching gene name or accession number or http://www.ncbi.nlm.nih.gov/nuccore by searching the accession number.

| Gene | Accession No. | SEQ ID NO: |
|---|---|---|
| AAEL012496 | XM_001662571 | 85 |
| AAEL004491 | XM_001649215 | 86 |
| AAEL007302 | XM_001652587 | 87 |
| AAEL007526 | XM_001652764 | 88, |
| | XM_001652765 | |
| AAEL007547 | XM_001658369 | 89 |
| AAEL007538 | XM_001658370 | 90 |
| AAEL007544 | XM_001658380 | 91 |
| AAEL007566 | XM_001658399 | 92 |
| AAEL007579 | XM_001658408 | 93 |
| AAEL007581 | XM_001658416 | 94 |
| AAEL007586 | XM_001658433 | 95 |
| AAEL007584 | XM_001658424 | 96 |
| AAEL007589 | XM_001658431 | 97 |
| AAEL007602 | XM_001658442 | 98 |
| AAEL007637 | XM_001658476 | 99 |
| AAEL001244 | XM_001658486 | 100 |

TABLE 5-continued

Additional larval lethal genes of the *Aedes* genus. All gene sequences can be found at www.vectorbase.org by searching gene name or accession number or http://www.ncbi.nlm.nih.gov/nuccore by searching the accession number.

| Gene | Accession No. | SEQ ID NO: |
|---|---|---|
| AAEL007660 | XM_001658506 | 101 |
| AAEL005271 | XM_001650568 | 102 |
| AAEL005975 | XM_001664278 | 103 |
| | XM_001664277 | |
| AAEL013809 | XM_001663948 | 104 |
| AAEL003051 | XM_001663042 | 105 |
| AAEL005816 | XM_001651417 | 106 |
| AAEL002932 | XM_001656111 | 107 |
| AAEL007742 | XM_001658562 | 108 |
| AAEL002137 | XM_001654794 | 109 |
| | XM_001654795 | |
| | XM_001654796 | |
| AAEL011432 | XM_001661601 | 110 |
| AAEL005359 | XM_001650724 | 111 |
| AAEL001698 | XM_001659907 | 112 |
| AAEL004165 | XM_001648513 | 113 |
| AAEL000822 | XM_001651235 | 114 |
| AAEL013892 | XM_001664046 | 115 |
| AAEL008578 | XM_001653263.1 | 116 |
| AAEL002848 | XM_001655976 | 117 |
| AAEL005895 | XM_001651523 | 118 |
| AAEL003517 | XM_001656855.1 | 119 |
| AAEL004344 | XM_001648893 | 120 |
| AAEL012107 | XM_001655804 | 121 |
| AAEL000584 | XM_001648604 | 122 |
| AAEL001574 | XM_001653540 | 123 |
| AAEL004707 | XM_001619561 | 124 |
| AAEL002348 | XM_001661305 | 125 |
| AAEL005507 | XM_001650968 | 126 |
| AAEL008058 | XM_001658821 | 127 |
| | XM_001658820 | |
| | XM_001658822 | |
| AAEL011527 | XM_001661684 | 128 |
| AAEL008696 | XM_001659375 | 129 |
| AAEL010850 | XM_001661051 | 130 |
| | XM_001661052 | |
| | XM_001661053 | |
| | XM_001661054 | |
| | XM_001661055 | |
| | XM_001661056 | |
| | XM_001661057 | |
| | XM_001661058 | |
| | XM_001661059 | |
| AAEL004371 | XM_001648944 | 131 |
| AAEL000763 | XM_001650931 | 132 |
| AAEL001876 | XM_001654103 | 133 |
| AAEL011447 | XM_001661620 | 134 |
| AAEL007546 | XM_001658390 | 135 |
| AAEL010506 | XM_001660834 | 136 |
| | XM_001660835 | |
| AAEL009430 | XM_001659998 | 137 |
| AAEL002761 | XM_001655903 | 138 |
| | XM_001655904 | |
| | XM_001655905 | |
| | XM_001655906 | |
| | XM_901655907 | |
| | XM_001655908 | |
| | XM_001655909 | |
| AAEL005211 | XM_001650462.1 | 139 |
| AAEL013159 | XM_001663290 | 140 |
| AAEL007538 | XM_001658370 | 90 |
| AAEL007605 | XM_001658438 | 141 |
| AAEL004166 | XM_001648524 | 142 |
| AAEL000242 | XM_001660084 | 143 |
| AAEL004600 | XM_001649385 | 144 |
| AAEL010488 | XM_001654556 | 145 |
| AAEL011279 | XM_001661515 | 146 |
| AAEL014566 | XM_001647781 | 147 |
| AAEL004688 | XM_001649545 | 148 |
| AAEL004942 | XM_001650039 | 149 |
| | XM_001650040 | |

TABLE 5-continued

Additional larval lethal genes of the *Aedes* genus. All gene sequences can be found at www.vectorbase.org by searching gene name or accession number or http://www.ncbi.nlm.nih.gov/nuccore by searching the accession number.

| Gene | Accession No. | SEQ ID NO: |
|---|---|---|
| AAEL009600 | XM_001660229 | 150 |
| AAEL002684 | XM_001662076 | 151 |
| AAEL004859 | XM_001649836 | 152 |
| AAEL002534 | XM_001655416 | 153 |
| AAEL002047 | XM_001654537 | 154 |
| AAEL011776 | XM_001661853 | 155 |
| AAEL006062 | XM_001651739 | 156 |
| AAEL011656 | XM_001661777 | 157 |
| AAEL009496 | XM_001660119 | 158 |
| AAEL000185 | XM_001658891<br>XM_001658892 | 159 |
| AAEL007049 | XM_001652493 | 160 |
| AAEL010226 | XM_001660647<br>XM_001660648 | 161 |
| AAEL005356 | XM_001650727 | 162 |
| AAEL003193 | XM_001656464<br>XM_001656465 | 163 |
| AAEL005454 | XM_001650853 | 164 |
| AAEL010063 | XM_001660545 | 165 |
| AAEL009898 | XM_001654041 | 166 |
| AAEL004546 | XM_001649342 | 167 |
| AAEL013236 | XM_001663353 | 168 |
| AAEL008741 | XM_001653377 | 169 |
| AAEL012171 | XM_001655866 | 170 |
| AAEL003908 | XM_001647954 | 171 |
| AAEL010387 | XM_001654441 | 172 |
| AAEL013221 | XM_001656454 | 173 |
| AAEL001440 | XM_001659262.1 | 174 |
| AAEL010059 | XM_001660555 | 175 |
| AAEL001101 | XM_001652364<br>XM_001652365 | 176 |
| AAEL012944 | XM_001663079<br>XM_001663080 | 177 |
| AAEL007718 | XM_001652797 | 178 |
| AAEL013795 | XM_001663931 | 179 |
| AAEL017156 | XM_011495422 | 180 |
| AAEL004526 | XM_001649284 | 181 |
| AAEL017349 | XM_011495018 | 182 |
| AAEL010048 | XM_001654123 | 183 |
| AAEL009829 | XM_001660391 | 184 |
| AAEL011782 | XM_001661856 | 185 |
| AAEL013002 | XM_001663144 | 186 |
| AAEL001324 | XM_001653011 | 187 |
| AAEL002411 | XM_001655165<br>XM_001655166 | 188 |
| AAEL000050 | XM_001647845 | 189 |
| AAEL010821 | XM_001654966 | 190 |
| AAEL003287 | XM_001663494<br>XM_001663495 | 191 |
| AAEL008461 | XM_001659198 | 192 |
| AAEL008220 | XM_001658989 | 193 |
| AAEL008656 | XM_001659346 | 194 |
| AAEL011070 | XM_001655039 | 195 |
| AAEL002062 | XM_001654551<br>XM_011494771 | 196 |
| AAEL007874 | XM_001652913 | 197 |
| AAEL000693 | XM_001650205 | 198 |
| AAEL007730 | XM_001658558 | 199 |
| AAEL008863 | XM_001653431 | 200 |
| AAEL007884 | XM_001652923 | 201 |
| AAEL012420 | XM_001655986 | 202 |
| AAEL004756 | XM_001649686 | 203 |
| AAEL005175 | XM_001650448 | 204 |
| AAEL012585 | XM_001656090<br>XM_001656090<br>XM_001656091 | 205 |
| AAEL011701 | XM_001655595 | 206 |

Table 6 provides additional larval lethal genes listed for *Aedes* and *Anopheles* genus, and includes specific siRNA targeted sequences within these genes that is conserved between both the *Aedes* and the *Anopheles* species. In some instances, the sequence targeted is also conserved in *Culex* mosquitoes.

TABLE 6

Additional siRNA sequences and corresponding genes

| *Aedes aegypti* Gene ID | *Anopheles gambiae* Gene ID | siRNA targeted Sequences | SEQ ID NO: |
|---|---|---|---|
| AAEL000014 | AGAP003349 | TACTATCACCTTGGTTATTGT | 207 |
| AAEL000528 | AGAP011320 | CCGTAAGGCCAGCAGTGTAGT | 208 |
| AAEL000704 | AGAP007942 | TTGTATGCTGAACCTAATAAT | 209 |
| AAEL002653 | AGAP008656 | TCCGTCACCGCGACGATAATT | 210 |
| AAEL004269 | AGAP007247 | CACTGCGCCTGCGGATCACAT | 211 |
| AAEL004313 | AGAP008822 | GTCGTGCTCGGCGATCATGTT | 212 |
| AAEL005451 | AGAP010163 | CCGGGAGCAGCGGATCTTGAA | 213 |
| AAEL005733 | AGAP010147 | TGCTGAGCTGGCGCTGGATGT | 214 |
| AAEL006901/ AAEL006898 | AGAP010242 | GTGATATGGCGAATTATTAAT | 215 |
| AAEL014564/ AAEL015302 | AGAP010307 | GCGTTGGCCTCGCTGTTAACT | 216 |
| AAEL008696 | AGAP009777 | CACCGACGCGCAGGTTCAACT | 217 |
| AAEL007874 | AGAP012189 | CTCGATGGGGCCCCACGATTT | 247 |
| AAEL001875 | AGAP010138 | TGCTGCGGTCGCAGATTGATT | 248 |
| AAEL000421 | AGAP002731 | ATGGCACCAGGCGTGATAGTT | 249 |
| AAEL004266 | AGAP007242 | ATCCGGAGCCGGTTTTGTTTA | 250 |
| AAEL002287 | AGAP000591 | GCCGGAGCGCCTCGATGCAGT | 251 |
| AAEL007526 | | CGGCTTCGTCGGCGAAACGTT | 252 |
| AAEL003875 | AGAP004438 | TTGAACCGGTTGCATGAAATT | 253 |
| AAEL004344 | AGAP011655 | GGGCGAGCGGGGCGAATGCAT | 254 |
| AAEL005400 | AGAP003893 | TGCCTCGAGCGGTGTTGTACT | 255 |
| AAEL007146, AAEL007143 | AGAP008200, AGAP008201 | ATGTAGTCGATGATATTTACA | 256 |
| AAEL007505 | AGAP005010 | CAGTCGCTGCCCGTTTGGTTT | 257 |
| AAEL010467 | AGAP002374 | ACCGAACCCGCGGCTACGCTT | 258 |
| AAEL011197, AAEL004631, AAEL005961 | AGAP005095, AGAP011516 | ACGGGGCCAGGGCGGTGATTT | 259 |
| AAEL014176 | AGAP004311 | GTCGACCACGCTGGTAAAGGT | 260 |
| AAEL000242 | AGAP000254 | AAGGAATGATTGCGATTATAT | 261 |
| AAEL000242 | AGAP000254 | TTGCTTGTTCGCCTAATTCAT | 262 |
| AAEL014915 | AGAP001651 | TCCGTGCACCGGCGTCACATT | 263 |
| AAEL017168 | AGAP006089 | TCGCTCCGCATCGCTACTATT | 264 |
| AAEL004006 | AGAP002974 | TCCCAACGCAAGGTATGATTA | 265 |
| AAEL002653 | AGAP008656 | CCGTCACCGCGACGATAATTA | 266 |
| AAEL017168 | AGAP006089 | CGCTCCGCATCGCTACTATTA | 267 |

TABLE 6-continued

Additional siRNA sequences and corresponding genes

| *Aedes aegypti* Gene ID | *Anopheles gambiae* Gene ID | siRNA targeted Sequences | SEQ ID NO: |
|---|---|---|---|
| AAEL002902 | AGAP011985 | ATCGCTCGGCAGCGTTGGAAT | 268 |
| AAEL004006 | AGAP002974 | AACGGCAGGCACCTTCATAAT | 269 |
| AAEL002653 | AGAP008656 | ATCCGTCACCGCGACGATAAT | 270 |
| AAEL014915 | AGAP001650, AGAP001651 | CTGGGCCAGCGCCTTCATGAT | 271 |
| AAEL003920 | AGAP004613 | TGCAGAACGCGGCGATGATAT | 272 |
| AAEL000242 | AGAP000254 | TCGAATGCCTAGATAATTTAA | 273 |
| AAEL000402 | AGAP011038 | GGCTTTCCTGGGCGGAGATCT | 274 |
| AAEL012925 | AGAP004405 | TACGCTGCAGGCAGGATTTGT | 275 |

Laboratory Biological Activity Assays

Following the identification of larval lethal genes in *A. coluzzii* and *A. aegypti*, siRNAs targeting the orthologs of these genes (vectorbase.org) in additional anopheline and aedine vector mosquito species are determined, particularly anopheline species that are endemic to the Gates foundation priority geographies of sub-Saharan Africa, the Greater Mekong Sub-region, and Hispaniola, as well as *Aedes albopictus*, which is broadly distributed in the United States and a vector for several disease-causing viruses, including Zika. Wherein it is possible, siRNAs corresponding to target sequences conserved in multiple species are tested. A guiding principle of these assays is to focus on siRNAs that have little potential for targeting genes in other animal species, which is examined through BLAST searches in sequenced genomes. siRNAs with high levels of homology to sequences in the human genome are eliminated. An advantage of using siRNA larvicides is that when resistance builds due to mutations in the sequence targeted, additional siRNAs corresponding to separate sequences within the same target gene can be used. Our goal is to identify 2-3 siRNA target sequences that are conserved in anopheline or aedine mosquitoes that result in significant lethality when targeted. Genes that can be effectively targeted with the smallest amount of siRNA are selected so as to increase the effectiveness and reduce the costs of this intervention. Fine-scale laboratory bioactivity analyses are then conducted for the most lethal siRNAs. These assays are being performed as described in the WHO (2005) guidelines for larvicide testing. Lethal concentrations (LC) for 50% (LC50) and 90% (LC90) mortality and inhibition of adult emergence (IE50 and IE90) are determined. Data are analyzed through Probit analysis with the POLO-PC program.

siRNA Delivery Strategies

There are several methods of interfering RNA delivery. These techniques, are summarized below:

Larval Soaking:

RNA interference was induced in *A. aegypti* mosquito larvae by soaking larvae in a solution of dsRNA for several hours (Singh et al., 2013). We have had similar success with siRNA in *A. aegypti* and have found that the siRNA soaking strategy also works in anopheline mosquitoes (MDS, unpublished). These laboratory experiments have been conducted using the Singh et al. (2012) protocol in conjunction with gene-specific 28-mer siRNAs at a concentration of 0.5 micrograms/microliter. siRNAs that kill up to 85% of larvae following a single four hour soaking treatment have been identified. These findings suggest that siRNA larvicides could be added directly to larval breeding sites.

Chitosan/siRNA nanoparticles: We have successfully used non-toxic chitosan nanoparticles for interfering RNA delivery to mosquito larvae (Mysore et al., 2013, 2014a, 2015; Zhang et al., 2015, see also video protocol at: jQve.com/video/52523/chitosaninterfering-mananoparticle-mediated-genesilencing-disease). Chitosan/siRNA nanoparticles are formed by self-assembly of polycations with interfering RNA through the electrostatic forces between positive charges of the amino groups in chitosan and negative charges carried by the phosphate groups on the backbone of interfering RNA. Chitosan is believed to enhance the stability and/or cellular uptake of dsRNA (Zhang et al., 2010). Chitosan/siRNA nanoparticles are mixed with larval food and then fed to larvae. This technique is relatively inexpensive, requires little equipment and labor, and facilitates high throughput analyses. Our experiments have demonstrated that chitosan/siRNA targeting larval lethal genes results in up to 50% mosquito larval lethality. These nanoparticles along with other nanoparticles known in the art may be used to target the delivery of the siRNA of the present technology.

Bacterial Delivery Systems:

*Bacillus thuringiensis* bacteria have been successfully used for mosquito larval control, making interfering RNA delivery through genetically modified microbes another potential option. Such a microbial delivery mechanism is attractive since it would significantly reduce the cost of this intervention by eliminating the need to purchase siRNA or synthesize it in vitro. Whyard et al. (2015) fed mosquito larvae dsRNA-expressing non-pathogenic *E. coli* mixed with larval food as bait. They obtained significant levels of knockdown—even when using heat killed bacteria. For proof of concept experiments, we are using the Whyard et al. (2015) approach for delivery of our siRNA larvicides. This strategy involves the use of nonpathogenic *E. coli* strain HT115-DE3 (obtained from the *Caenorhabditis* Genetics Center, University of Minnesota, USA) which is transformed with the dsRNA transcription plasmid pL4440 (obtained from Addgene, Cambridge, Mass., USA) containing a fragment of the gene of interest or GFP (control). Expression plasmids and bacteria feeding lines are prepared as described (Silencing Genomes, 2006) and then fed to larvae as discussed by Whyard et al. (2015). Both live bacteria and heat-killed bacteria are being assessed in our laboratory experiments. Our preliminary data suggest that this microbial delivery system provides an effective means of delivering interfering RNA larvicides. We have observed up to 100% larval death/failure to pupariate—even when the bacteria are heat-killed prior to treatment of mosquitoes. The plasmid-based expression system described above is appropriate for simulated field, semi-field, and small-scale field studies.

For large-scale field studies, dsRNA expression cassettes would be integrated into the bacterial genome, which eliminates risks of horizontal gene transfer or introduction of any antibiotic resistance marker genes carried on plasmids.

Yeast Delivery System:

Van Ekert et al. (2014) silenced *A. aegypti* larval genes by feeding them nonpathogenic *Pichia pastoris* yeast expressing a long hairpin RNA (lhRNA) sequence corresponding to the gene to be silenced. In collaboration with Na Wei (University of Notre Dame), we are conducting laboratory experiments to explore the use of this delivery system. For proof of concept experiments, we are using the Van Ekert (2014) delivery protocol with the following modifications: i)

we are using *Saccharomyces cerevisiae*, non-pathogenic baker's yeast that is commonly used in baking and beverage production, ii) we are using short hairpin RNAs (shRNAs), a short artificial RNA molecule with a hairpin turn that can be used to silence gene expression through RNAi. The short sequence of these shRNAs, which correspond to the sequences of our siRNA larvicides, is preferable to lhRNAs, which have a higher risk of off-species targeting than shorter shRNA molecules. iii) As with the bacterial studies, both live and heat-killed yeast are assessed. *Saccharomyces cerevisiae* is an appealing delivery system, as mosquito larvae are highly attracted to yeast and will ingest it directly. Moreover, the yeast can be dried and packaged much in the same manner in which it is sold commercially, which would greatly facilitate the distribution of interfering RNA yeast larvicides. In one embodiment, the yeast is heat-killed and dried into a pellet formulation that is fed to larvae and has shown success in killing larvae.

Finally, as is the case for bacterial delivery systems, use of yeast is expected to significantly decrease the costs of siRNA production since shRNA expression is easily amplified through yeast cultivation. We have cloned inserts designed to produce shRNA corresponding to larval lethal genes into the pRS426 GPD bacteria/yeast shuttle vector (Mumberg et al., 1995). Yeast expressing these hairpins have been tested as described by Van Ekert et al. (2014) and according to the WHO (2005) protocol. Our preliminary data suggest that ingestion of yeast interfering RNA larvicides generates up to 100% larval death/failure to pupariate even when the yeast are heat-killed.

As with the bacterial studies, the yeast plasmid-based expression system described above is appropriate for simulated field, semi-field, and smallscale field studies. For large-scale field studies, advanced genome editing techniques such as CRISPR/Cas9 will facilitate stable and seamless genome integration of shRNA expression cassettes, which eliminates risks of horizontal gene transfer or introduction of any antibiotic resistance marker genes.

Stable Yeast Delivery System

The inventors have integrated the shRNA expression cassette into the *S. cerevisiae* genome to allow for stable expression of the siRNA in the years. Further, the expression of the shRNA was placed under the control of an inducible promoter. Generation of stable transformants was performed by DNA encoding shRNA corresponding to sequences #1 and #3 in Table 2 was ligated downstream of the Gal1 promoter (Bassel and Mritmer, 1971; Douglas and Condie, 1954, incorporated by reference in their entireties) and upstream of the cycl terminator. The resulting Gal1 promoter-shRNA-cycl terminator expression cassettes were cloned into the multiple cloning sites of pRS404 and pRS406 (Sikorski and Hieter, 1989, incorporated by reference in their entireties), yeast integrating plasmid shuttle vectors bearing TRP1 and URA3 markers, respectively. The resulting plasmids were used for genome integration of the shRNA expression cassettes at the trp1 and ura3 loci of the *S. cerevisiae* CEN.PK strain (genotype=MATa/α ura3-52/ura3-52 trp1-289/trp1-289 leu2-3_112/leu2-3_112 his3 Δ1/his3 Δ1 MAL2-8C/MAL2-8C SUC2/SUC2) (van Dijken et al., 2000, incorporated by reference in its entirety). Stable transformants were selected by growth on synthetic complete media lacking tryptophan or uracil. Integration events at both loci were confirmed via PCR and sequencing.

Generation of these stable transformants eliminates the use of plasmids with antibiotic resistance markers and the potential for horizontal transfer of shRNA expression cassettes.

Algal Delivery System:

Microorganisms, including microalgae, serve as a primary source of nutrition for mosquito larvae (Merritt et al., 1992). Kumar et al. (2013) described a microalgal-based system for delivery of interfering RNA to mosquito larvae. They silenced *Anopheles stephensi* larval genes by feeding them *Chlamydomonas reinhardtii* expressing a hairpin sequence corresponding to the gene to be silenced. We have separately confirmed that *A. aegypti* larvae will eat *Chlamydomonas* in a laboratory setting and believe that these microalgae can be used to deliver shRNA to *A. aegypti* larvae. For proof of concept experiments, using the GeneArt *Chlamydomonas* Engineering Kit (Invitrogen Life Technologies), we will clone inserts designed to produce shRNA corresponding to larval lethal genes into the pChlamy_3 shuttle vector. These constructs are used to transform algae. Algal interfering RNA larvicides are tested on mosquito larvae as described by Kumar et al. (2013). This system can be evaluated in simulated field, semifield, and in field experiments. As with the bacterial and yeast studies, the *Chlamydomonas* plasmid-based expression system described above is appropriate for simulated field, semi-field, and small-scale field studies. For large-scale field studies, hairpin expression constructs are integrated into the *Chlamydomonas reinhardtii* chloroplast genome as described by Economou et al. (2014). Use of algal species that are native to field sites in which the interfering RNA insecticides are used can also be used, preferably those that are normally ingested by mosquitoes. To this end, we are collecting larval specimens from the field to evaluate the algal species that they consume in the wild.

Field Studies

Simulated Field Studies:

Simulated field trials are conducted in the Scheel laboratory according to the WHO (2005) guidelines. In summary, each control/experimental condition is tested on 100 third instar larvae in 5 L tubs containing 2 L water, larval food, and covered with nylon mesh. Mortality is assessed at 2, 4, and 7 days. Four replicates are performed for control and experimental conditions, and data are analyzed through Analysis of Variance (ANOVA). The effects of bacteria, yeast, algae or chitosan delivering interfering RNA targeting high priority genes of interest are being assessed, as will the larval soaking delivery strategy. Experiments are performed at 26° C. (typical insectary temperature) and 32° C. (typical daytime temperature in tropical climates).

Semi-Field Studies

Rooftop semi-field experiments are conducted at the Galvin Life Science Center, University of Notre Dame, Ind. They have established a semi-field larvicide test site which can be used to evaluate our siRNA larvicides and delivery strategies. We have conducted semi-field studies in collaboration with David Chadee at his rooftop laboratory at the University of the West Indies, St. Augustine, Trinidad and Tobago. In all locations, these studies are conducted as described in the WHO (2005) larvicide testing guidelines, which follow the simulated field trial methodology discussed above (IV), except that the studies are conducted outdoors and on natural mosquito populations (for the Kenya and Trinidad and Tobago studies). The effects of bacteria, yeast, algae or chitosan delivering interfering RNA targeting high priority genes of interest are assessed, as will the larval soaking delivery strategy.

Figure 3:
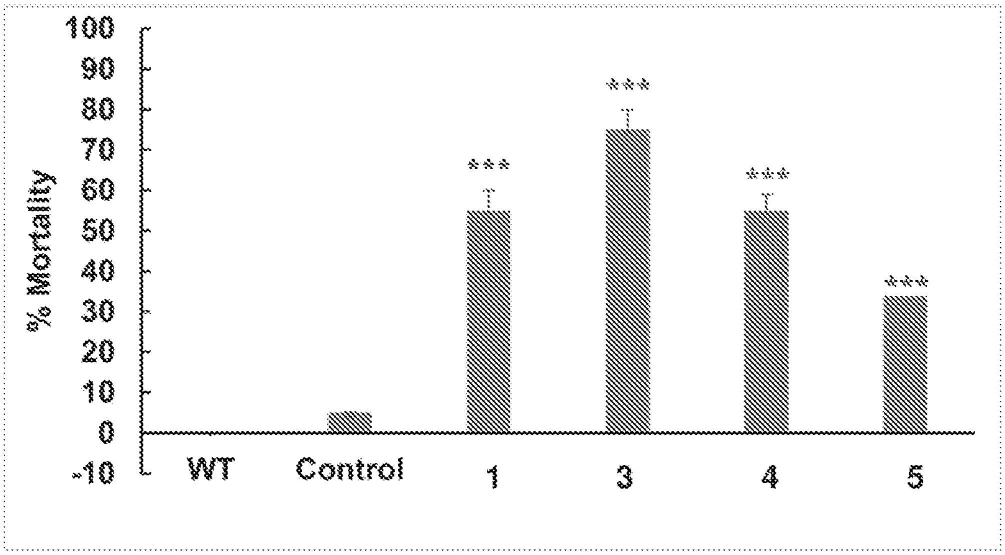
FIG. 3 is a bar graph representing larval mortality following brief exposure to siRNA of the present invention in semi-field trials.

A semi-field test was performed with *A. aegypti* eggs collected from oviposition cups in Trinidad. siRNA (#1 targeting AAEL007292 (SEQ ID NO:1), #3 targeting AAEL007298, #4 targeting AAEL007563, and #5 targeting AAEL004756 (SEQ ID NO: 12) were delivered through larval soaking for three hours as described above, after which time larvae were reared under semi-field conditions. This brief exposure to all of the siRNAs assayed induced significant $p<0.001$) larval mortality in comparison to control siRNA-treated or wild-type (WT) untreated animals. Results compiled from four replicate experiments is shown in FIG. 3, each with 20/larvae/condition are shown. Error bars represent standard errors of the mean.

Field Trials:

Larvicide field assays are conducted in Belize, Thailand, Kenya and Trinidad and Tobago. Guiyun Yan's laboratory has described several potential field sites in Kenya (Kweka et al., 2012). The proposed field site in Trinidad and Tobago is an area south of Sangre Grande toward the northeast corner of the island, in Guiaco Tamana District. The site is located on an isolated stretch along Los Armadillos Road. The area around the site is completely forested for several kilometers. The Severson and Chadee labs have performed larval sampling experiments at this site, where they have found an abundance of *A. aegypti* larvae. We are conducting field trials in several locations throughout Belize, including the Belize Vector and Ecology Center Field Station. Sites in Thailand, including the Kamphaeng Phet and Kanchanaburi field sites, are selected for testing of the siRNA and compositions of the present invention.

Small Scale Field Trials:

Small scale field trials are conducted on natural mosquitoes located in natural breeding sites. The objectives of these studies are to: i) determine the efficacy, including residual activity of interfering RNA larvicides in natural breeding sites, ii) identify the optimum field application dosage, iii) monitor abiotic parameters which may impact the efficacy of the larvicides, and to iv) record qualitative observations of non-target biota cohabitating with mosquito larvae (WHO, 2005). Specific interfering RNA larvicides and delivery strategies deemed to be suitable in our simulated field and semi-field experiments are assessed in the field. The habitats to be evaluated in these experiments include natural and man-made containers that are not used to store drinking water. As discussed in the WHO guidelines (2005), at least three replicates of each type of habitat are randomly selected for each dosage of the experimental or control larvicide formulation. Post-treatment immature (first and second instar, third and fourth instar, and pupal) abundance are monitored in samples taken just prior to treatment, on day 2, and then weekly until the density of fourth instar larvae in treated habitats is comparable to that of the control containers. Efficacy and residual activity are ascertained through measurement of the pre- and post-treatment abundance of each larval instar and pupae, accounting for the dynamics of change occurring in the treated and control containers. Adult emergence are monitored by sampling and counting pupal skins. Data are assessed as described in the WHO (2005) guidelines using ANOVA.

Large Scale Field Trials:

The efficacy of larvicides deemed acceptable in small field trials is verified in larger scale field trials conducted according to the WHO (2005) guidelines on natural mosquito populations located in natural breeding habitats. The objectives of these trials include: i) confirmation of the efficacy of the larvicide at the selected field application dosage when applied to large-scale plots in natural breeding habitats, ii) verification of larvicide residual activity and application intervals, iii) examination of the ease of larvicide application and dispersal, iv) assessment of community acceptance of this intervention, and v) detection of any unanticipated effects of the treatment on non-targeted organisms (WHO, 2005). Pretreatment densities of larvae and pupae are assessed in each larval habitat at least twice over the course of a week prior to treatments. The habitats to be evaluated include those assessed in the small scale field trials, but 25 replicates of each habitat are assessed for each control or experimental treatment. Samples are taken and assessed and data evaluated using the same general procedure described for the small scale trials. Nontarget organisms cohabitating with mosquito larvae are also be counted and examined to ascertain unanticipated impacts of the larvicide treatments. Furthermore, the ease of storage, handling, and application of the insecticide formulation are assessed. Observations on the acceptability of these larvicides to residents of the area will also be recorded.

Example 2: Bacteria Interfering RNA Larvicides

Figure 4:
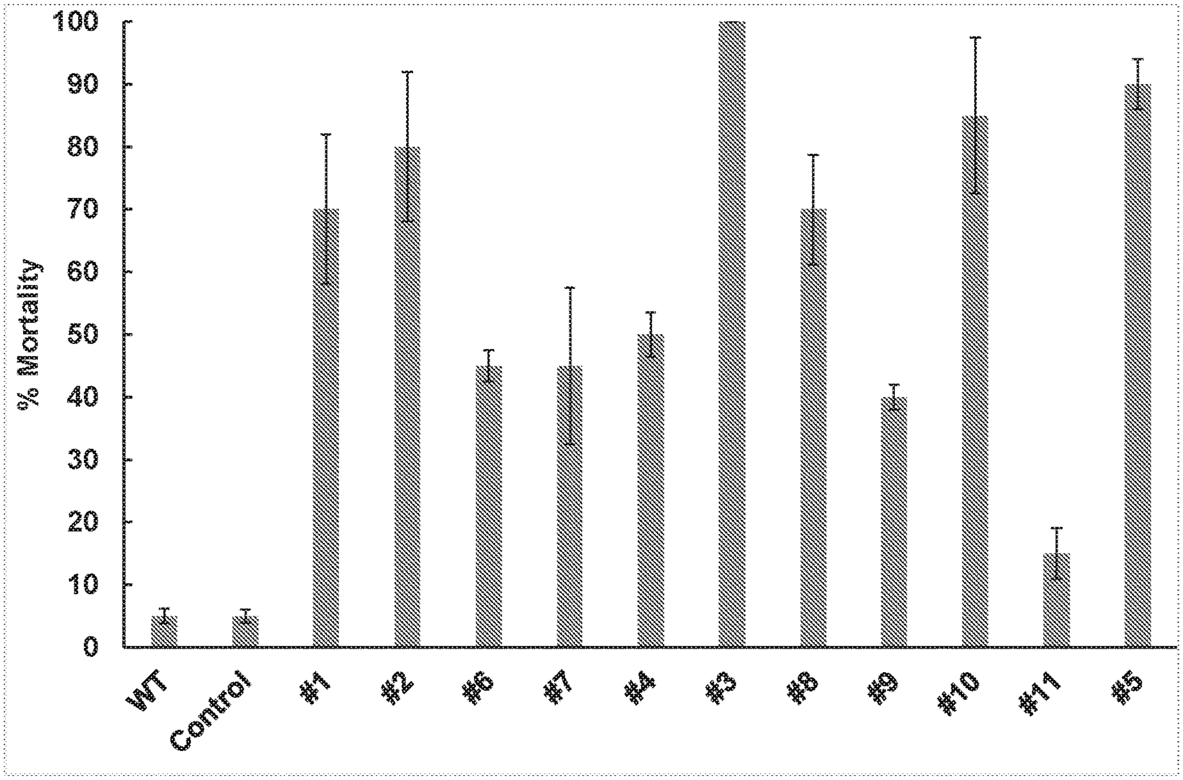
FIG. 4 is a bar graph depicting larval mortality induced by bacteria interfering RNA larvicides of the present invention.

*E. coli* expressing interfering RNA were prepared as described in Whyard et al (2015). Interfering RNA used were #1 targeting AAEL007292, #2 targeting AAEL007548, #3 targeting AAEL007298, #4 targeting AAEL007563, #5 targeting AAEL004756, #6 targeting AAEL007546, #7 targeting AAEL007554, #8 targeting AAEL007876, #9 targeting AAEL009273, #10 targeting AAEL007718, #11 targeting AAEL004874. Bacteria was heat inactivated and fed on larvae for three days post-hatching. Larvae fed with bacteria expressing dsRNA corresponding to GFP (control) survived (no significant differences were detected in comparison to wild-type (WT) larvae fed a normal laboratory diet. Larval mortality was significantly higher in bacteria #11 vs control-fed larvae ($p<0.01$). All other bacteria interfering RNA larvicides induce very highly significant ($p<0.001$) larval mortality levels. Results compiled from at least four replicate experiments is shown in FIG. 4, each with 20 larvae/condition. Error bars represent standard errors of the mean.

Example 3: Preparation of *S. cerevisiae* Expressing shRNA

Our laboratories and others have experimented with dsRNA delivery strategies that could potentially be implemented in the field. For example, we have successfully used non-toxic chitosan nanoparticles, natural carbon based materials that promote dsRNA stability and uptake, to deliver siRNA to *A. aegypti* larvae (Zhang et al., 2015). While this technique is effective, we have begun to explore microbial delivery systems for interfering RNA delivery. Such systems would be advantageous, as they would reduce costs associated with synthesis or purchase of interfering RNA. Whyard et al. (2015) used live or heat-killed orally delivered non-pathogenic *E. coli* expressing dsRNA to silence *A. aegypti* larval genes, and we have successfully employed their technique in *A. aegypti*, confirming that it is possible to use a microbial interfering RNA delivery system for larval lethal gene silencing in mosquitoes. While we have had success with this technique, it requires that the bacteria be mixed with yeast bait. Likewise, chitosan nanoparticles must also be mixed with yeast as bait. Thus, it would be advantageous to simply express the interfering RNA directly in yeast. Moreover, as discussed above, *S. cerevisiae* can be dried, packaged, and shipped, which would facilitate international shipment. These advantages indicate that yeast may be an ideal delivery system.

In bacteria, dsRNA was produced through cloning target sequences into dsRNA transcription plasmid pL4440 (Addgene), a plasmid with T7 promoters located on either side of a multiple cloning site. However, use of such vectors in the field may raise concerns regarding the potential for horizontal transfer of such plasmids, which also bear antibiotic resistance markers.

We therefore use yeast to express shRNA, an artificial RNA molecule with a hairpin turn that can be used to silence gene expression through RNAi. Whyard et al. (2015) showed that both live and heat-killed *E. coli* give comparable results, and we have confirmed this result. The release of heat-killed yeast may be deemed more environmentally-friendly, and therefore both live and heat-killed yeast are assessed.

Target site selection: Input sequences for shRNA design correspond to the siRNAs used to target the 10 genes noted in Table 1, as well as to the sequence of an siRNA control (Tomchaney et al., 2014; Mysore et al., 2015) that lacks significant sequence homology within the *A. aegypti* genome. BlastN searches will be used to confirm that all of these *A. aegypti* target sequences have minimal sequence homology to genes in humans or other non-targeted organisms, thereby reducing the potential for off-species targeting. Additionally, we will use Scott Emrich's algorithm, a derivative of the program used in Tomchaney et al. (2014), to identify additional target sequences within these ten genes that are conserved among disease vector mosquitoes, including the closely-related disease vector mosquito *A. albopictus*, but not other species, including humans. These additional siRNAs will be assessed through microinjection and soaking per the protocols described above. Target sequences that are poorly conserved outside of mosquitoes, but that result in high levels of mortality when targeted in *A. aegypti*, will be assessed in yeast. We will identify at least two such sequences for each gene. This will be useful if yeast interfering RNA larvicides were to one day be employed for vector control; if insecticide resistance were to develop due to a point mutation in one target sequence, then the second sequence can be targeted.

shRNA expression: For initial laboratory experiments, DNA cassettes corresponding to shRNA for each of the target sequences identified will be cloned into p426 GPD (ATCC® 87361™), a bacteria-yeast shuttle vector that allows for constitutive expression of inserts cloned downstream of a GPD promoter (Mumberg et al., 1995). shRNA DNA cloning cassettes will be designed using the Clonetech shRNA Sequence Designer Tool.

(Clonetech, 2015). Custom DNA oligos obtained from Invitrogen were annealed to generate shRNA DNA cloning cassettes that will be inserted into the multiple cloning site downstream of the GPD promoter. Appropriate restriction enzyme overhangs were added to the DNA cassettes to facilitate cloning. Following yeast transformation, shRNA expression will be confirmed through qRT-PCR, which will be performed as described (Hayes et al., 2011) using real-time quantification with the SYBR Green I PCR kit and a Step One Plus System (Applied Biosystems). Following sequencing to confirm the sequences of the inserts, the plasmids will be transformed into *S. cerevisiae* strain BY4742.

Preliminary data: We have successfully cloned silencing hairpins corresponding to AAEL007292 and AAEL007548 (Table 1), as well as a control hairpin in this manner. Our preliminary analysis of yeast transformed with these experimental constructs demonstrates that they are larvicidal as demonstrated in FIG. 2 and FIG. 5.

Generation of stable transformants: Following larvicide testing, DNA cassettes for expressing shRNAs with larvicidal activity are inserted into the yeast genome to generate stable transformants using the general methodology described by Wei et al. (2015). Advanced genome editing techniques such as CRISPR/Cas9 will facilitate stable and seamless genome integration of the DNA cassettes, which eliminates risks of horizontal gene transfer or introduction of any antibiotic resistance marker genes (DiCarlo et al., 2013; Hsu et al., 2014). shRNA expression will be verified as described above.

Figure 2:
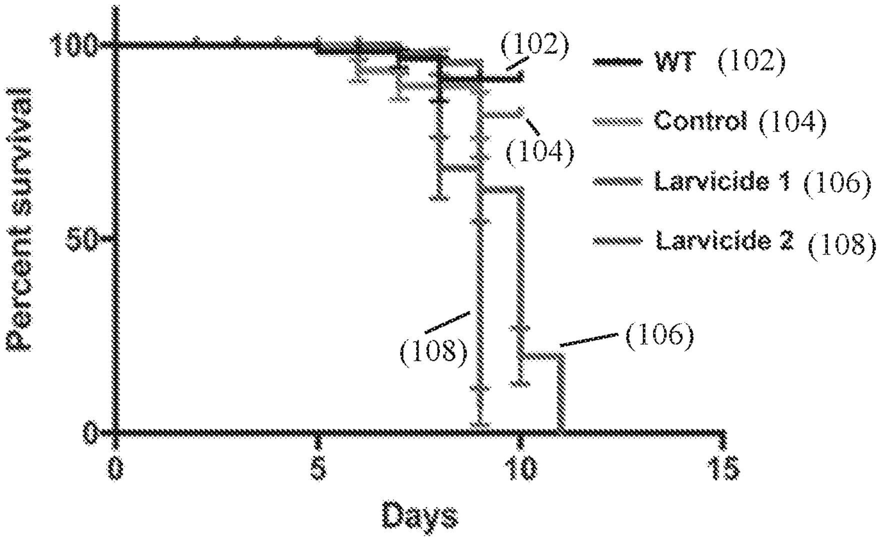
FIG. 2 depicts the results of yeast interfering RNA larvicide trial. Larvicide assays were conducted with yeast expressing shRNA corresponding to target sequences in AAEL007292, AAEL007548, or to a control sequence that lacked significant homology in the *A. aegypti* genome. A second control group was fed only wild type (WT) yeast. Assays were performed with 20 larvae. Yeast larvicides targeting AAEL007292 (Larvicide 1) and AAEL007548 (Larvicide 2) resulted in mortality within six days.
Figure 5:
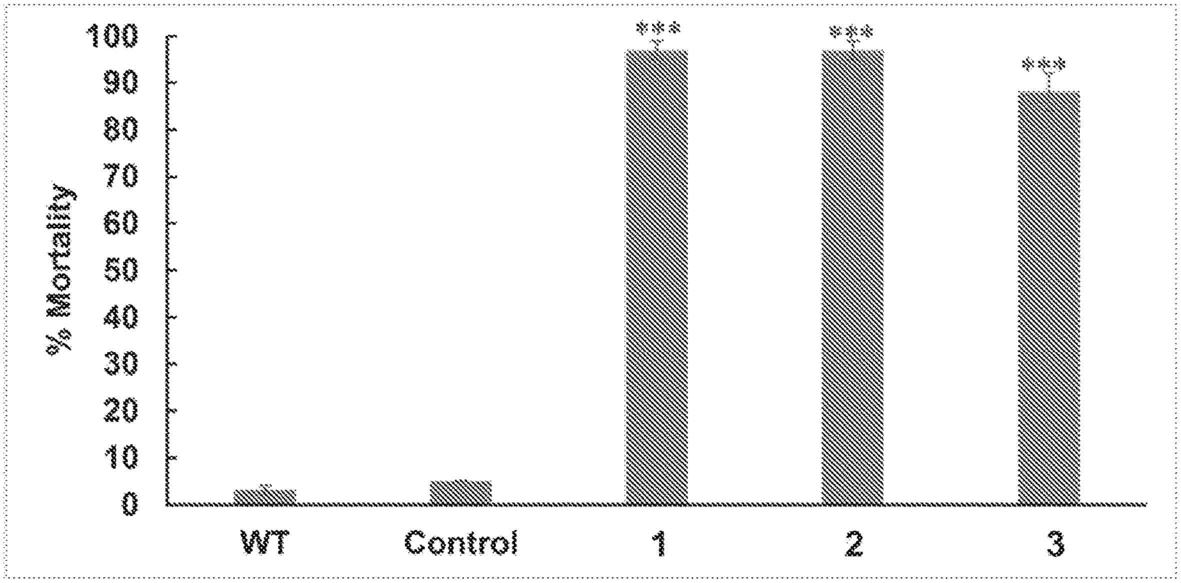
FIG. 5 is a bar graph depicting the larval mortality induced by heat-inactivated yeast containing the siRNA of the present invention.

Yeast Larvicide Studies:

i. Animal rearing: The *A. aegypti* Liverpool-IB12 (LVP-IB12) strain from which the current genome sequence (Nene et al., 2007) was generated was used and reared as described (Clemons et al., 2010b). We have also used *A. aegypti* eggs collected from oviposition traps in Trinidad and are using *A. aegypti* strains maintained at the Belize Vector and Ecology field station. A. *coluzzii* were obtained from Nora Besansky. *A. gambiae* were obtained from the MR4 Facility. For larvicide assays, larvae are reared in accordance with WHO guidelines for larvicide testing (WHO, 2005; see details below). Larvicides will also be tested on the *A. aegypti* Rockefeller strains.

ii. Small scale studies: 30 first instar larvae are transferred to 500 mL plastic cups with 100 mL water and reared at 26° C. Larvae are allowed to feed at will on yeast expressing control or experimental shRNA. In these and all of the experiments described below, both live and heat-killed yeast are assessed. Dead larvae that do not respond to probing will be removed daily. Mortality is assessed daily. Pupariation and adult emergence rates are also be assessed at week's end. Experiments are performed a minimum of three times, and ANOVA is used for data analysis. Trials conducted in this manner with yeast interfering RNA larvicides targeting AAEL007292 and AAEL007548 (see Table 1) shows that these larvicides are highly effective at inducing mortality in small scale laboratory studies. A representative trial is shown in FIG. 2. FIG. 5 also demonstrate the results, showing heat-inactivated yeast are able to kill *Aedes aegypti*. FIG. 5 demonstrates the results of laboratory larval feeding experiments with heat-inactivated yeast interfering RNA larvicides #1 (targeting AAEL007292), #2 (targeting AAEL007548), and #3 (targeting AAEL000032) are shown. Nearly all larvae fed with yeast larvicides #1 and #2 for the first three days post-hatching died as larvae, while larvae fed a normal laboratory diet (WT) or with yeast expressing shRNA with no known *Aedes* target (Control) survived. Yeast larvicide #3 also induced very significantly high levels of mortality. Results compiled from at least three replicate experiments, each with 20 larvae/condition, are shown. For larvicides #1 and #2, 100% of the larvae died in two of the three replicate experiments. Error bars represent standard errors of the mean. ***=$p<0.001$ in comparison to control-treated larvae. We have also found that three yeast interfering RNA larvicides targeting *Anopheles coluzzii* genes induced 100% larval mortality when animals were fed either live or heat-killed yeast (FIG. 6).

Microbial Interfering RNA Larvicides Targeting Anopheline Mosquitoes.

Figure 6:
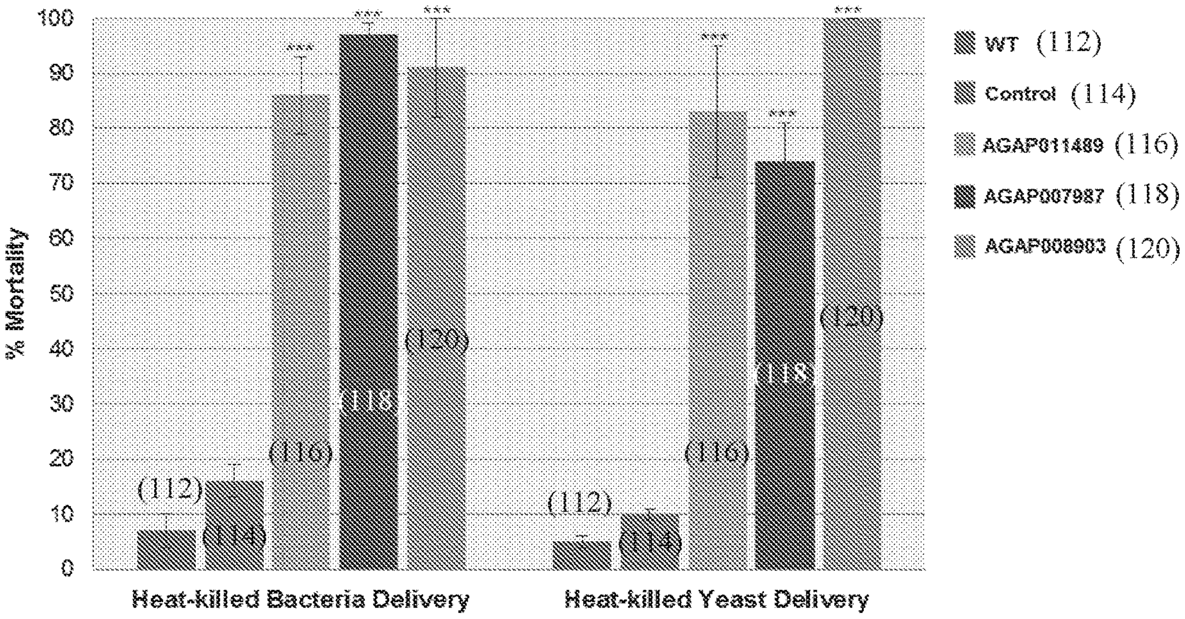
FIG. 6 is a graph showing the percent larval mortality induced by heat-inactivated bacteria or heat-inactivated yeast.

As shown in FIG. 6, *E. coli* producing dsRNA corresponding to target sequences in larval lethal genes identified in the Anopheline screen induced significant larval mortality (Left: AGAP011489, AGAP007987, or AGAP008903 dsRNA vs. control dsRNA, $p<0.001$). Also shown in FIG. 6, *S. cerevisiae* producing shRNA corresponding to the same target sequences also induced significant larval mortality (Right: AGAP011489, AGAP007987, or AGAP008903 dsRNA vs. control hairpin, $p<0.001$). Bacteria and yeast were heat-killed prior to larval feedings.

In addition to assessing mortality, silencing of the targeted genes is verified and quantified through qRTPCR. qRT-PCR is performed using real-time quantification with the SYBR Green I PCR kit and a Step One Plus System (Applied Biosystems) as described in Clemons et al. (2011). At least three biological replicates are conducted, and PCR reactions will be performed in triplicate. Quantification of results are made by standardizing reactions to levels of the housekeeping gene RPS17 (Morlais et al., 2003) and using the AACt method. Data will be evaluated with the Student's t-test.

Adult Mosquito Lethality Screen.

Target genes identified as larval lethal genes identified herein are further screened to identify target genes that are also adult lethal. Adult mosquitoes are starved for 12 hours and then fed ad libitum for 12 hours with 100 nM siRNA dissolved in 5% sucrose solution delivered to mosquitoes on cotton wicks. Food dye is added to the solution for confirmation of successful feeding. For the screen, two replicate experiments with 20 mosquitoes per treatment are assessed. Adult death is monitored for 1, 3, and 5 days following treatment, and data is analyzed with ANOVA.

siRNA SEQ ID Nos:1 and 3 were found to be adult lethal in addition to larvae lethal. 70% of animals fed ad libitum for 4 hrs with 100 nM siRNA #1 died, and 44% of animals fed with 100 nM siRNA #3 died.

The present invention is not intended to be limited to the foregoing examples, but encompasses all such modifications and variations as come within the scope of the appended claims.

All references cited are incorporated by reference in their entireties.

REFERENCES

1. Clemons, A., Haugen, M., Severson, D., and M. Duman-Scheel (2010). "Functional analysis of genes in *Aedes aegypti* embryos." Cold Spring Harb Protoc 2010(10): pdb prot5511.
2. Economou, C., Wannathong T., Szaub, J., and Purton, S. "A simple, low-cost method for chloroplast transformation of the green alga *Chlamydomonas reinhardtii*." Pal Maliga (ed.), Chloroplast Biotechnology: Methods and Protocols, Methods in Molecular Biology, 1132: 401-411.
3. Kumar, A., Wang, S., Ou, R., Samrakandi, M., Beerntsen, B. T., and Sayre, R. T. (2013). Development of an RNAi based microalgal larvicide to control mosquitoes. MW Journal. 4:6 (GCE Special Issue).
4. Kweka, E. J., Zhou, G., Munga, S., Lee, M. C., Atieli, H. E., Nyindo, M., Githeko, A. K., and Yan, G. (2012). Anopheline larval habitats seasonality and species distribution: a prerequisite for effective targeted larval habitats control programmes. PLoS One. 7(12):e52084.
5. Merritt, R. W. (1992). "Feeding behaviour, natural food, and nutritional relationships of larval mosquitoes." Ann. Rev. Entomol. 37: 349-376.
6. Mumberg, D., Muller, R., and Funk, M. (1995). "Yeast vectors for the controlled expression of heterologous proteins in different genetic backgrounds." Gene 156: 119-122.
7. Mysore, K., E. M. Flannery, M. Tomchaney, D. W. Severson and M. Duman-Scheel (2013). "Disruption of *Aedes aegypti* olfactory system development through chitosan/siRNA nanoparticle targeting of semaphorin-1a." PLoS Negl Trop Dis 7(5): e2215.
8. Mysore, K., E. Andrews, P. Li and M. Duman-Scheel (2014a). "Chitosan/siRNA nanoparticle targeting demonstrates a requirement for single-minded during larval and pupal olfactory system development of the vector mosquito *Aedes aegypti*." BMC Dev Biol 14: 9.
9. Mysore, K., E. Flannery, M. T. Leming, M. Tomchaney, L. Shi, L. Sun, J. E. O'Tousa, D. W. Severson and M. Duman-Scheel (2014b). "Role of semaphorin-la in the developing visual system of the disease vector mosquito *Aedes aegypti*." Dev Dyn 243(1 1): 1457-69. Silencing Genomes (2006). "Creating an RNAi feeding strain." silencinggenomes.org/downloads/pdfs/rnai_feeding_ strain.pdf, accessed 6/2015.
10. Singh, A. D., Wong, S., Ryan, C. P., and Whyard, S. Oral delivery of double-stranded RNA in larvae of the yellow fever mosquito, "*Aedes aegypti*: Implications for pest mosquito control." J Insect Sci 13: 69.
11. Van Ekert, E., C. A. Powell, R. G. Shatters Jr., and D. Borovsky. "Control of larval and egg development in *Aedes aegypti* with RNA interference against juvenile hormone acid methyl transferase." J Insect Physiol 70: 143-150. WHO (2005). "Guidelines for laboratory and field testing of mosquito larvicides." http://whglibdoc.who.int/hq/2005/who_cds whopes_gcdpp_2005.13.pdf, accessed September 2014.
12. Whyard, S., C. N. Erdelyan, A. L. Partridge, A. D. Singh, N. W. Beebe, and R. Capina (2015). "Silencing the buzz: a new approach to population suppression of mosquitoes by feeding larvae double-stranded RNAs." Parasit Vectors 8: 96.
13. Zhang, X., J. Zhang and K. Y. Zhu (2010). "Chitosan/double-stranded RNA nanoparticle mediated RNA interference to silence chitin synthase genes through larval feeding in the African malaria mosquito (*Anopheles gambiae*)." Insect Mol Biol 19(5): 683-693.
14. Zhang, X., K. Mysore, E. Flannery, K. Michel, D. W. Severson, K. Y. Zhu, and M. Duman-Scheel. "Chitosan/interfering RNA nanoparticle mediated gene silencing in disease vector mosquito larvae." J Vis Exp 97: doi: 10.3791/52523.
15. Anderson E A, Birmingham A, Baskerville S, Reynolds A, Maksimova E, Leake D, Federov Y, Karpilow J, Khovorova A. Experimental validation of the importance of seed complement frequency to siRNA specificity. RNA 14:853-861, 2008.
16. Altschul S F, Gish W, Miller W, Myers E W, Lipman D J. Basic local alignment search tool. J. Mol. Biol. 215: 403-410, 1990.
17. Custom DsiRNA Design Tool, IDT, Coralville, USA. Retrieved Jun. 23, 2016. idtdna.com/Scitools.
18. Doench J G, Petersen C P, Sharp P A. siRNAs can function as miRNAs. Genes & Development 17:438, 2003.
19. Ichihara M, Murakumo Y, Masuda A, Matsuura T, Asai N, Jijiwa M, Ishida M, Shinmi J, Yatsuya H, Qiao S, Takahashi M, Ohno K. Thermodynamic instability of siRNA duplex is a prerequisite for dependable prediction of siRNA activities. Nucleic Acids Res 35:e123, 2007.
20. Judge A D, Sood V, Shaw J R, Fang D, McClintock K, MacLachlan I. Sequence-dependent stimulation of the mammalian innate immune response by synthetic siRNA. Nature Biotechnology 23(4):457, 2005.
21. Kamola P J, Nakano Y, Takahashi T, Wilson P A, Ui-Tei, K. The siRNA non-seed region and its sequences are auxillary determinants of off-target effects. PLOS Computational Biology 11(12):e1004656, 2015.
22. Naito Y, Yoshimura J, Morishita S, Ui-Tei K. siDirect 2.0: updated software for designing functional siRNA with reduced seed-dependent off-target effect. BMC Bioinformatics 10:392, 2009.

23. Ui-Tei K, Naito Y, Nishi K, Juni A, and Saigo K. Thermodynamic stability and Watson-Crick base pairing in the seed duplex are major determinants of the efficiency of the siRNA based off-target effect. Nucleic Acids Research 36(22):7100, 2008.
24. Wee L M, Flores-Jasso F, Salomon W E, Zamore P D. Argonaute divides its RNA guide into domains with distinct functions and RNA-binding properties. Cell 151: 1055, 2012.
25. Bassel, J. and Mortimer, R. (1971). Genetic order of the galactose structural genes in *Saccharomyces cerevisiae*. J Bacteriol 108(1):179-83.
26. Douglas, H. C. and Condie, F. (1954). The genetic control of galactose utilization in *Saccharomyces*. J Bacteriol 68(6):662-70.
27. Sikorski, R. S., Hieter, P. (1989). A system of shuttle vectors and yeast host strains designed for efficient manipulation of DNA in *Saccharomyces cerevisiae*. Genetics 122: 19-27.
28. Van Dijken, J. P., Bauer, J., Brambilla, L., Duboc, P., Francois, J. M., Gancedo, C., Giuseppin, M. L. F., Heijnen, J. J., Hoare, M., Lange, H. C., Madden, E. A., Niederberger, P., Nielsen, J., Parrou, J. L., Petit, T., Porro, D., Reuss, M., van Riel, N., Rizzi, M., Steensma, H. Y., Verrips, C. T., Vindelov, J., and Pronk, J. T. (2000). An interlaboratory comparison of physiological and genetic properties of four *Saccharomyces cerevisiae* strains. Enzyme Microb. Technol. 26:706-714. DOI: 10.1016/S0141-0229(00)00162-9.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11252965B2). An electronic copy of the "Sequence Listing" will also be available from the USPTO upon request and payment of the fee set forth in 37 CFR 1.19(b)(3).

We claim:

1. An interfering ribonucleic acid (iRNA) comprising a nucleobase sequence of 21 nucleotides that that is perfectly complementary to the nucleobase sequence of one of SEQ ID NO: 261, SEQ ID. NO: 262, and SEQ ID. NO: 273, wherein the iRNA is capable of inhibiting the expression of *Aedes aegypti* Gene ID AAEL000242 by RNA interference.

2. The iRNA of claim 1, wherein the iRNA is a small interfering RNA (siRNA), a short hairpin RNA (shRNA), double stranded RNA (dsRNA), an RNA construct, or an anti-sense oligonucleotide.

3. A DNA construct that encodes and can express the iRNA of claim 1.

4. A yeast, bacterial, algal, or plant cell engineered to produce at least one iRNA according to claim 1.

5. A mosquito-ingestible composition comprising (i) the iRNA of claim 1, (ii) a bacterial cell, a yeast cell, an algal cell, or a plant cell expressing the iRNA, or (iii) the DNA construct of claim 3, and at least one suitable carrier, excipient, or diluent.

6. The mosquito-ingestible composition of claim 5, wherein the composition comprises the yeast cell.

7. The mosquito-ingestible composition of claim 5, wherein the yeast cell is heat inactivated.

8. A method for inhibiting the expression of *Aedes aegypti* Gene ID AAEL000242, or an ortholog thereof, by RNA interference comprising exposing at least one mosquito larva or adult to the interfering ribonucleic acid (iRNA) according to claim 1 in an effective amount to inhibit the expression of the gene or ortholog, wherein the ortholog comprises a nucleobase sequence that is at least 85% identical to the entire length of SEQ ID NO: 261, 262, or 272.

9. The method of claim 8, wherein the at least one mosquito larva comprises larvae from two or more mosquito species.

10. The mosquito-ingestible composition of claim 5, wherein the composition comprises:

a) a yeast cell engineered to produce the iRNA;

b) a bacterial cell engineered to produce the iRNA; or c) an algal or plant cell engineered to produce the iRNA.

11. The mosquito-ingestible composition of claim 10, wherein the iRNA is an shRNA.

12. The composition of claim 10 further comprising a sugar bait optionally including nanoparticles, yeast, bacteria, or a combination thereof.

13. The composition of claim 10 further comprising a dried inactivated yeast.

14. The mosquito-ingestible composition of claim 5, wherein the mosquito-ingestible composition is formulated as a sugar bait composition or as a chitosan nanoparticle composition, optionally wherein the sugar bait composition or chitosan nanoparticle composition comprises yeast, bacteria, or both yeast and bacteria.

* * * * *